(12) United States Patent
Danvy et al.

(10) Patent No.: US 6,436,973 B1
(45) Date of Patent: Aug. 20, 2002

(54) LTA$_4$ HYDROLASE INHIBITORS

(75) Inventors: Denis Danvy, Yvetot; Thierry Monteil, Saint Georges sur Fontaine; Jean-Christophe Plaquevent, Notre-Dame de Bondeville; Pierre Duhamel; Lucette Duhamel, both of Mont-Saint-Aignan; Nadine Noel, Moernach; Claude Gros, Paris; Olivier Chamard, Lyons; Jean-Charles Schwartz; Jeanne-Marie Lecomte, both of Paris, all of (FR)

(73) Assignees: Bioprojet; Institut National de la Sante et de la Recherche Medicale (Inserm), Paris (FR)

( * ) Notice: Subject to any disclaimer, the term of this patent is extended or adjusted under 35 U.S.C. 154(b) by 0 days.

(21) Appl. No.: 09/787,708

(22) PCT Filed: Sep. 21, 1999

(86) PCT No.: PCT/FR99/02240
§ 371 (c)(1),
(2), (4) Date: Jun. 11, 2001

(87) PCT Pub. No.: WO00/17133
PCT Pub. Date: Mar. 30, 2000

(30) Foreign Application Priority Data

Sep. 21, 1998 (FR) .............................. 98 11758

(51) Int. Cl.$^7$ .................. C07D 213/64; C07C 323/25; A61K 31/44
(52) U.S. Cl. ................. 514/357; 514/438; 514/465; 514/643; 514/657; 546/334; 549/78; 549/434; 564/305; 564/315
(58) Field of Search .................. 546/334; 514/357, 514/438, 465, 643, 657; 549/78, 434; 564/305, 315

(56) References Cited

FOREIGN PATENT DOCUMENTS

FR 2604434 A * 4/1998
WO WO 96300314 * 3/1996

OTHER PUBLICATIONS

Qian et al, J. Med. Chem, vol. 39, No. 1, pp. 217–223, 1996.*
Fournie–Zaluski et al, J. Med. Chem, vol. 35, No. 7, pp. 1259–1266, 1992.*
Kohama et al, Chem. Pharm. Bulletin, vol. 40, No. 2, pp. 414–418, 1992.*

* cited by examiner

Primary Examiner—Zinna Northington Davis
(74) Attorney, Agent, or Firm—Larson & Taylor PLC

(57) ABSTRACT

The invention concerns LTA$_4$ hydrolase inhibiting compositions of formula (1) as set forth below. It also concerns their therapeutic, in particular anti-inflammatory, applications.

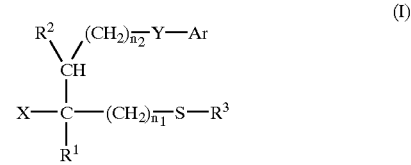

48 Claims, No Drawings

LTA₄ HYDROLASE INHIBITORS

CROSS-REFERENCE TO RELATED APPLICATIONS

This application is a 371 application of PCT/FR99/02240 filed Sep. 21, 1999.

The invention relates to compounds as defined hereinafter, which constitute a class of medicaments having mainly an anti-inflammatory activity and/or acting by inhibiting $LTA_4$ (leukotriene $A_4$) hydrolase, an enzyme which is responsible for the biosynthesis of leukotriene $LTB_4$, a major proinflammatory mediator.

It also relates to such compounds useful for forming prodrugs.

It also relates to methods for preparing these compounds.

$LTA_4$ hydrolase (EC 3.3.2.6.) is an enzyme which is in particular present in the neutrophils and whose sequence has been recently shown (Funck et al., P.N.A.S., 1987, 89: 6677) to be related to that of a zinc metallopeptidase, aminopeptidase M (Malfroy et al., B.B.R.C., 1989, 161: 236). In agreement with the suggestion by Malfroy et al., it has been recognized that $LTA_4$ possesses a zinc atom which is essential for its catalytic activity, an aminopeptidase-type activity, and is sensitive to the action of certain metallopeptidase inhibitors (Heggstrom et al., B.B.R.C., 1990, 173: 431; Minami et al., B.B.R.C., 1990, 173: 620).

The inhibition of $LTA_4$ hydrolase is capable of preventing formation of $LTB_4$, a mediator responsible for the adhesion of the neutrophils to the endothelial cells and for their chemotaxis. It appears to be involved in the aetiology or the symptomatology of a variety of conditions and inflammatory states such as rheumatoid arthritis, chronic inflammations of the intestine, multiple sclerosis, gout and psoriasis. In these processes, $LTB_4$ is thought to act in synergy with other metabolites of arachidonic acid which are produced by 5-lipoxygenase or cyclooxygenases whose inhibition is well known to produce anti-inflammatory effects.

Some $LTA_4$ hydrolase inhibiting compounds have been described, in particular in patent applications WO 94/00420, WO 96/11192, WO 96/10999 and WO 96/27585.

The objective of the present invention is to provide novel compounds capable of inhibiting $LTA_4$ hydrolase.

The objective of the present invention is also to provide compounds which can be used as medicaments.

To this end, the subject of the invention is compounds of formula (I) as defined below.

Its subject is also pharmaceutical compositions containing at least one such compound.

Its subject is also the use of compounds of formula (I) as defined below, as medicaments which act as inhibitor of the activity of $LTA_4$ hydrolase, in particular as anti-inflammatory agents.

The subject of the invention is also the use of compounds of formula (I) in the form of prodrugs.

The inventors have demonstrated that the compounds of formula (I), or their salts obtained with therapeutically acceptable inorganic or organic acids or their stereoisomers, possessed an $LTA_4$ hydrolase inhibiting activity.

The compounds (I) according to the invention have, moreover, good bioavailability.

The present invention describes a series of compounds capable of potently inhibiting $LTA_4$ hydrolase.

These compounds have, in addition, a biological activity as indicated below, which makes them therapeutically useful.

The compounds according to the invention correspond to the following formula (I):

$$\begin{array}{c} R^2 \diagdown \diagup (CH_2)_{\overline{n_2}} Y - Ar \\ CH \\ | \\ X - C - (CH_2)_{\overline{n_1}} S - R^3 \\ | \\ R^1 \end{array} \quad (I)$$

in which:

X is chosen from the following groups:
  i) $-NH_2$ ii)
  $$-N= \diagup\diagdown \begin{array}{c} R^4 \\ R^5 \end{array}$$

$R^1$ and $R^2$ are independently chosen from the following groups:
  i) a hydrogen atom
  ii) a lower alkyl group
  iii a lower alkyl group substituted with a halogen atom
  iv) $CF_3$
  v) a halogen atom;
$n_1$ varies from 1 to 4
$n_2$ varies from 0 to 10
$R^3$ is chosen from the following groups:
  i) a hydrogen atom ii)
  $$-\underset{\underset{O}{\|}}{C}-NH-R^6$$

iii)
  $$-\underset{\underset{O}{\|}}{C}-R^6$$

iv)
  $$-S-(CH_2)_{\overline{n_1}}\underset{\underset{R^1}{|}}{\overset{\overset{R^2\diagdown \diagup(CH_2)_{\overline{n_2}}Y-Ar}{CH}}{C}}-X$$

v)
  $$-S\diagdown\diagup\underset{NH_2}{\overset{COOH}{|}}$$

Y is chosen from the following groups:
  i) $-O-$
  ii) $-CH_2-$
  iii) $-S-$
  iv) $-OCH_2-$
  v) $-SCH_2-$
  vi) $-NH-$
Ar is chosen from the following groups:
  i) a phenyl group which is unsubstituted or which is mono- or polysubstituted with substituents chosen from halogen atoms and $CF_3$, lower alkyl, lower alkoxy, $NH_2$, $NO_2$, CN, OH, $CO_2H$, OPh, $OCH_2Ph$, SMe, SEt, Ph, $CH_2Ph$ and $NHCOR^7$ groups where $R^7$ is a lower alkyl group,

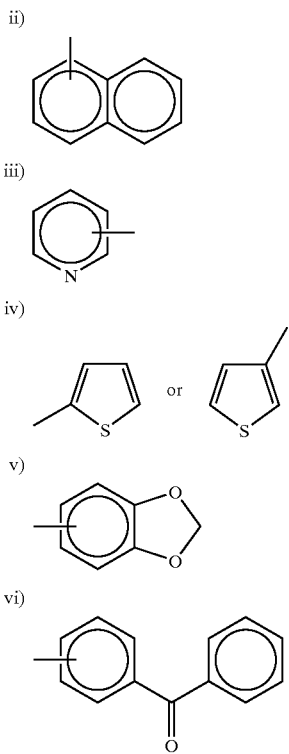

ii)

iii)

iv)

v)

vi)

$R^4$ and $R^5$ are independently chosen from the following groups: an unsubstituted phenyl group, a phenyl group which is mono- or polysubstituted with substituents chosen from halogen atoms and $CF_3$, $NO_2$, CN, OH, lower alkyl and lower alkoxy groups;

$R^6$ represents a lower alkyl group or a phenyl group.

The expression lower alkyl group is understood to mean an alkyl group having a linear or branched chain containing form 1 to 6 carbon atoms, such as methyl, ethyl, propyl, butyl, pentyl, hexyl and their branched isomers.

The expression lower alkoxy group is understood to mean an alkoxy group containing a linear or branched chain having 1 to 6 carbon atoms, such as methoxy, ethoxy, propoxy, butoxy, pentoxy, hexoxy and their branched isomers.

The halogen atoms are preferably chosen from chlorine and fluorine.

When a bond is drawn through a bond in a ring, this indicates that the bond may be linked to any available atom in this ring.

The invention also comprises the isomers of the compounds of formula (I), including the diastereoisomeric and enantiomeric forms.

The invention also extends to the therapeutically acceptable salts of these compounds, as well as to the salts of their isomers, including the diastereoisomeric and enantiomeric forms.

The expression therapeutically acceptable salts is understood to mean a salt which does not adversely affect either the chemical structure or the pharmacological properties of the compounds of the present invention. Such salts include inorganic or organic anions such as hydrochloride, hydrobromide, acetate, trifluoroacetate, maleate, fumarate, oxalate and the like, which are well known in the art. These salts are prepared in a conventional manner by neutralizing the compounds of formula (I) with the desired acid.

Among the compounds of formula (I) which is cited above, those for which X represents $NH_2$ and/or $R^3$ represents a hydrogen atom are preferred.

In this group, the compounds of formula (I) in which X is $NH_2$ and $R^3$ is a hydrogen atom are more particularly preferred.

The compounds of formula (I) for which $R^1$ represents a hydrogen atom also constitute a particularly preferred subgroup according to the invention.

The compounds of formula (I) with $R^1$ different from hydrogen represent another subgroup according to the invention.

A subfamily among the abovementioned compounds is formed by the compounds for which $n_1$ is equal to 1.

Another subfamily consists of the compounds for which $n_1$ is different from 1.

In accordance with the invention, $R^2$ preferably represents a hydrogen atom.

Another subgroup of compounds according to the invention is formed by the compounds where $R^2$ is different from a hydrogen atom. In this case, $R^2$ preferably represents a methyl group.

A subclass of compounds according to the invention also consists of those for which $n_2$ is equal to zero. Among these compounds, Y preferably represents —O—, —S—, —OCH$_2$—, —SCH$_2$— or —NH—.

Another subclass is formed by the compounds for which $n_2$ varies from 1 to 4, preferably from 2 to 4, and in a more particularly preferred manner by the compounds where $n_2$ is equal to 3.

Another class of compounds according to the invention is defined by those where $n_2$ is greater than 4.

From the point of view of the symbol Y, the compounds for which the latter represents an oxygen atom are particularly preferred according to the invention.

Other subfamilies may be defined according to whether Y represents —CH$_2$—, a sulphur atom, a group —CH$_2$— or —SCH$_2$— or alternatively a unit —NH—.

Ar is preferably chosen from a phenyl group which is unsubstituted or substituted, more preferably monosubstituted, with one of the abovementioned substituents.

When Ar symbolizes a substituted phenyl group, the substituent(s) are preferably chosen from halogen atoms, $CF_3$, lower alkyl, O(lower alkyl), $NO_2$, CN, $CO_2H$, OPh, OCH$_2$Ph, Ph and CH$_2$Ph groups, the halogen atoms as well as the lower alkyl and O(lower alkyl) groups being more particularly preferred.

The compounds for which Ar is a phenyl group which is mono- or polysubstituted with —OPh, —OCH$_2$Ph, —Ph or —CH$_2$Ph constitute another subfamily according to the invention.

Other subclasses are also defined according to whether Ar represents a naphthyl, pyridinyl or benzodioxazole group.

For all the abovementioned subfamilies, the substituents not specified may vary according to their respective general definitions.

A particularly preferred group of compounds according to the invention consists of the compounds corresponding to the following formula (II):

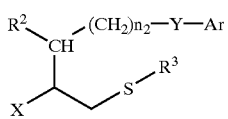

(II)

in which X, R², R³, Y, Ar and n₂ have the above meanings.

The preferences indicated above for the compounds of formula (I) also apply to those of formula (II).

A group which is even more particularly preferred comprises the compounds corresponding to the following formula (III):

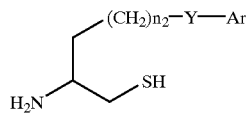

(III)

in which Y, Ar and n₂ have the meaning indicated above.

The particular choices mentioned for the compounds of formula (I) from the point of view of the symbols Y and Ar also apply to the compounds of formula (III).

Among the compounds of formula (II) or (III), those for which n₂ is equal to 3, Y represents an oxygen atom and Ar represents a phenyl group which is unsubstituted or substituted as indicated above, where appropriate R² representing a methyl group and R³ representing the unit iv) mentioned above, are particularly preferred according to the invention.

Examples of compounds of the present invention are:

(S)-2-amino-3-phenoxy-1-propanethiol hydrochloride
(S)-2-amino-3-benzyloxy-1-propanethiol hydrochloride
(R)-2-amino-3-benzyloxy-1-propanethiol hydrochloride
(2S,3R)-2-amino-3-methyl-3-benzyloxy-1-propanethiol hydrochloride
(2R,3S)-2-amino-3-methyl-3-benzyloxy-1-propanethiol hydrochloride
(S)-2-amino-3-benzylthio-1-propanethiol hydrochloride
(R,S)-2-amino-7-phenyl-1-heptanethiol hydrochloride
(R,S)-2-amino-2-methyl-6-phenoxy-1-hexanethiol hydrochloride
(S)-2-amino-3-(4-benzylphenoxy)-1-propanethiol hydrochloride
(R,S)-2-amino-4-phenyl-1-butanethiol hydrochloride
(R,S) -2-amino-6-phenoxy-1-hexanethiol hydrochloride
(R,S)-2-amino-7-phenoxy-1-heptanethiol hydrochloride
(R,S)-2-amino-7-(4-methoxyphenoxy)-1-heptanethiol hydrochloride
(R,S)-2-amino-6-(4-methoxyphenoxy)-1-hexanethiol hydrochloride
(R,S)-2-amino-6-(4-methylphenoxy)-1-hexanethiol hydrochloride
(R,S)-2-amino-6-(3-methylphenoxy)-1-hexanethiol hydrochloride
(R,S)-2-amino-6-(3-methoxyphenoxy)-1-hexanethiol hydrochloride
(R,S)-2-amino-6-(4-chlorophenoxy)-1-hexanethiol hydrochloride
(R,S)-2-amino-6-(4-bromophenoxy)-1-hexanethiol hydrochloride
(R,S)-2-amino-6-(4-fluorophenoxy)-1-hexanethiol hydrochloride
(R,S)-2-amino-6-(2-methoxyphenoxy)-1-hexanethiol hydrochloride
(R,S)-2-amino-6-phenylthio-1-hexanethiol hydrochloride
(R,S)-2-amino-6-(3,4-dioxymethylenephenoxy)-1-hexanethiol hydrochloride
(R,S)-2-amino-6-(4-ethoxyphenoxy)-1-hexanethiol hydrochloride
(R,S)-2-amino-6-(4-ethylphenoxy)-1-hexanethiol hydrochloride
(R,S)-2-amino-5-phenyl-1-pentanethiol hydrochloride
(R,S)-2-amino-4-phenoxy-1-butanethiol hydrochloride
(R,S)-2-amino-6-phenyl-1-hexanethiol hydrochloride
(R,S)-2-amino-4-phenylthio-1-butanethiol hydrochloride
(R,S)-2-amino-6-(2,6-dimethylphenoxy)-1-hexanethiol hydrochloride
(R,S)-2-amino-4-benzylthio-1-butanethiol hydrochloride
(R,S)-2-amino-5-phenoxy-1-pentanethiol hydrochloride
(R,S)-2-amino-6-(2-methylphenoxy)-1-hexanethiol hydrochloride
(R,S)-2-amino-6-(4-phenoxyphenoxy)-1-hexanethiol hydrochloride
(R,S)-2-amino-6-(4-carboxyphenoxy)-1-hexanethiol hydrochloride
(R,S)-2-amino-6-(4-cyanophenoxy)-1-hexanethiol hydrochloride
[2(R,S)-3(R,S)]-2-amino-3-methyl-6-phenoxy-1-hexanethiol hydrochloride
(R S)-2-amino-6-(4-phenylphenoxy)-1-hexanethiol hydrochloride
(R,S)-2-amino-6-(4-benzyloxyphenoxy)-1-hexanethiol hydrochloride
(R,S)-2-amino-6-(2-naphthyloxy)-1-hexanethiol hydrochloride
(R,S)-2-amino-6-(1-naphthyloxy)-1-hexanethiol hydrochloride
(R,S)-2-amino-8-phenoxy-1-octanethiol hydrochloride
(R,S)-2-amino-9-phenoxy-1-nonanethiol hydrochloride
(R,S)-2-amino-6-(3-trifluoromethylphenoxy)-1-hexanethiol hydrochloride
(R,S)-2-amino-6-(3-fluorophenoxy)-1-hexanethiol hydrochloride
(R,S)-2-amino-6-(2,4-difluorophenoxy)-1-hexanethiol hydrochloride
(R,S)-2-amino-6-(2-fluorophenoxy)-1-hexanethiol hydrochloride
(R,S)-2-amino-6-pentafluorophenoxy-1-hexanethiol hydrochloride
(R,S)-2-amino-6-(4-nitrophenoxy)-1-hexanethiol hydrochloride
(R,S)-2-amino-8-phenyl-1-octanethiol hydrochloride
(R,S)-2-amino-6-(3,5-dimethoxyphenoxy)-1-hexanethiol hydrochloride
(R,S)-2-amino-6-(4-butoxyphenoxy)-1-hexanethiol hydrochloride
(R,S)-2-amino-6-(4,5-dichlorophenoxy)-1-hexanethiol hydrochloride
(R,S)-2-amino-6-(2-pyridoxy)-1-hexanethiol hydrochloride
(R,S)-2-amino-6-(3-cyanophenoxy)-1-hexanethiol hydrochloride
(R,S)-2-amino-5-(4-benzylphenoxy)-1-pentanethiol hydrochloride
(R,S)-2-amino-6-(3-chlorophenoxy)-1-hexanethiol hydrochloride
(R,S)-2-amino-7-(4-cyanophenoxy)-1-heptanethiol hydrochloride
(R,S)-2-amino-5-(4-cyanophenoxy)-1-pentanethiol hydrochloride
(R,S)-2-amino-6-(3-ethylphenoxy)-1-hexanethiol hydrochloride
(R,S)-2-amino-6-(4-trifluoromethylphenoxy)-1-hexanethiol hydrochloride (R,S)-2-amino-7-(4-benzylphenoxy)-1-heptanethiol hydrochloride
(R,S)-2-amino-6-(4-benzylphenoxy)-1-hexanethiol hydrochloride
(R,S)-2-amino-5-(3-ethylphenoxy)-1-pentanethiol hydrochloride
(R,S)-2-amino-5-(4-methylphenoxy)-1-pentanethiol hydrochloride
(R,S)-2-amino-6-(4-acetamidophenoxy)-1-hexanethiol hydrochloride
(R,S)-2-amino-6-(4-iodophenoxy)-1-hexanethiol hydrochloride
(R,S)-2-amino-6-(4-propoxyphenoxy)-1-hexanethiol hydrochloride
(R,S)-2-amino-5-(4-benzoylphenoxy)-1-pentanethiol hydrochloride
(R,S)-2-amino-5-(4-ethoxyphenoxy)-1-pentanethiol hydrochloride
(R,S)-2-amino-7-(4-ethoxyphenoxy)-1-heptanethiol hydrochloride
(+)-2-amino-6-(4-ethoxyphenoxy)-1-hexanethiol hydrochloride
(−)-2-amino-6-(4-ethoxyphenoxy)-1-hexanethiol hydrochloride
(+)-2-amino-6-phenoxy-1-hexanethiol hydrochloride
(−)-2-amino-6-phenoxy-1-hexanethiol hydrochloride.

The compounds of formula (I) or (II) as defined above with

and/or $R^3$ different from the hydrogen atom, that is to say chosen from the groups ii)

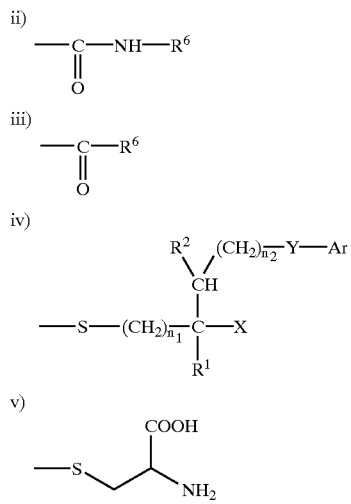

constitute prodrugs.

Among these compounds, those of the disulphide type, in particular with $R^3$ representing the group iv) above, are preferred prodrugs.

Examples of prodrugs according to the invention are:

1,1-dithiobis(2-(R,S)-amino-6-phenoxyhexane) dihydrochloride
(R,S)-2-amino-6-phenoxy-1-S-acetylthiohexane hydrobromide 1,1-dithiobis(2-(+)-amino-6-phenoxyhexane) dihydrochloride (A isomer)
1,1-dithiobis(2-(−)-amino-6-phenoxyhexane) dihydrochloride (B isomer)
1,1-dithiobis(2-(R,S)-amino-6-(4-ethoxyphenoxy)-1-hexane) dihydrochloride
1,1-dithiobis(2-(+)-amino-6-(4-ethoxyphenoxy)-1-hexane) dihydrochloride (A isomer)
1,1-dithiobis(2-(−)-amino-6-(4-ethoxyphenoxy)-1-hexane) dihydrochloride (B isomer)
1,1-dithiobis(2-(R,S)-amino-6-(4-acetamidophenoxy)-1-hexane dihydrochloride
1,1-dithiobis(2-(R,S)-amino-6-(4-cyanophenoxy)-1-hexane dihydrochloride.

The compounds of the present invention are prepared from easily available raw materials according to one of the methods indicated below.

The reaction schemes given below describe methods which may be used for the preparation of the compounds of formula (I), indicating the starting materials, the intermediates as well as the synthesis conditions.

The abbreviations used in the present description correspond to the definitions below:

Ac: acetyl
Bn: benzyl
DCC: dicyclohexylcarbodiimide
DEAD: diethyl azodicarboxylate
DIAD: diisopropyl azodicarboxylate
DMF: dimethylformamide
DPPA: diphenylphosphoryl azide
Et: ethyl
EtOH: ethyl alcohol
$Et_2O$: ethyl ether
HOBT: hydroxybenzotriazole
LAH: lithium aluminium hydride
Me: methyl
Ms: methanesulphonyl
n.Bu: n-butyl
$NBu_4F$: butylammonium fluoride
$NEt_3$: triethylamine
n.Pr: n-propyl
Pd/C: palladium on carbon
Ph: phenyl
tBu: tert-butyl
TFA: trifluoroacetic acid
THF: tetrahydrofuran
Ts: para-toluenesulphonyl Schemes 1 to 3 describe the preparation of substituted amino alcohols.

Scheme 1

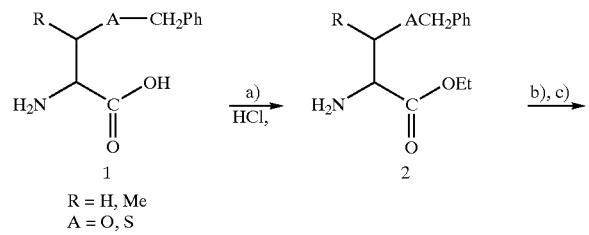

R = H, Me
A = O, S

a) SOCl₂, EtOH, reflux
b) Net₃, Et₂O, CHCl₃
c) LAH, Et₂O

Scheme 1 describes a method for preparing the compounds of formula 3 from commercial amino acids.

Compounds 2 are easily obtained by esterification, in the presence of thionyl chloride and EtOH, of the amino acid 1. The amino alcohol 3 is obtained in 2 steps after releasing the amine with NEt₃ and then reducing with LAH in Et₂O at room temperature.

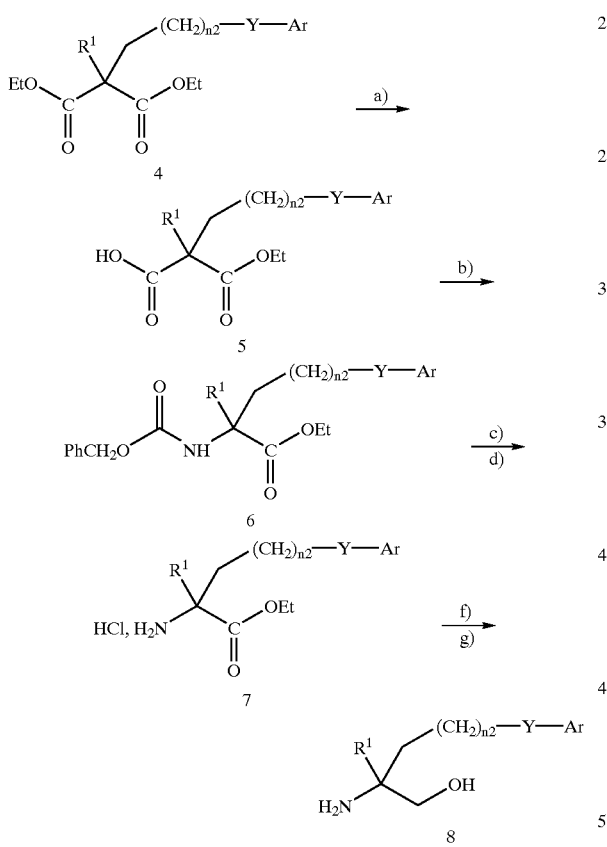

$R^1$, n2, Y and Ar are as defined in formula (I).
a) KOH, EtOH, 0° C.
b) DPPA, NEt₃, toluene, benzyl alcohol, 80° C.
c) H₂, Pd/C, EtOH
d) HCl 3N
f) NEt₃, Et₂O, CHCl₃
g) LAH, Et₂O The malonates of formula 4 are obtained by alkylating a malonate with the corresponding brominated or chlorinated derivatives in the presence of sodium ethoxide in ethanol under reflux. Monosaponification using a solution of KOH in EtOH gives the compounds 5 which are subjected to a Curtius reaction in the presence of DPPA, NEt₃ and benzyl alcohol in toluene at 80° C. overnight.

The benzyloxycarbonyl functional group is deprotected by catalytic hydrogenation in ethanol using Pd/C to give the amino esters 7. The amino alcohols 8 are obtained as described in scheme 1.

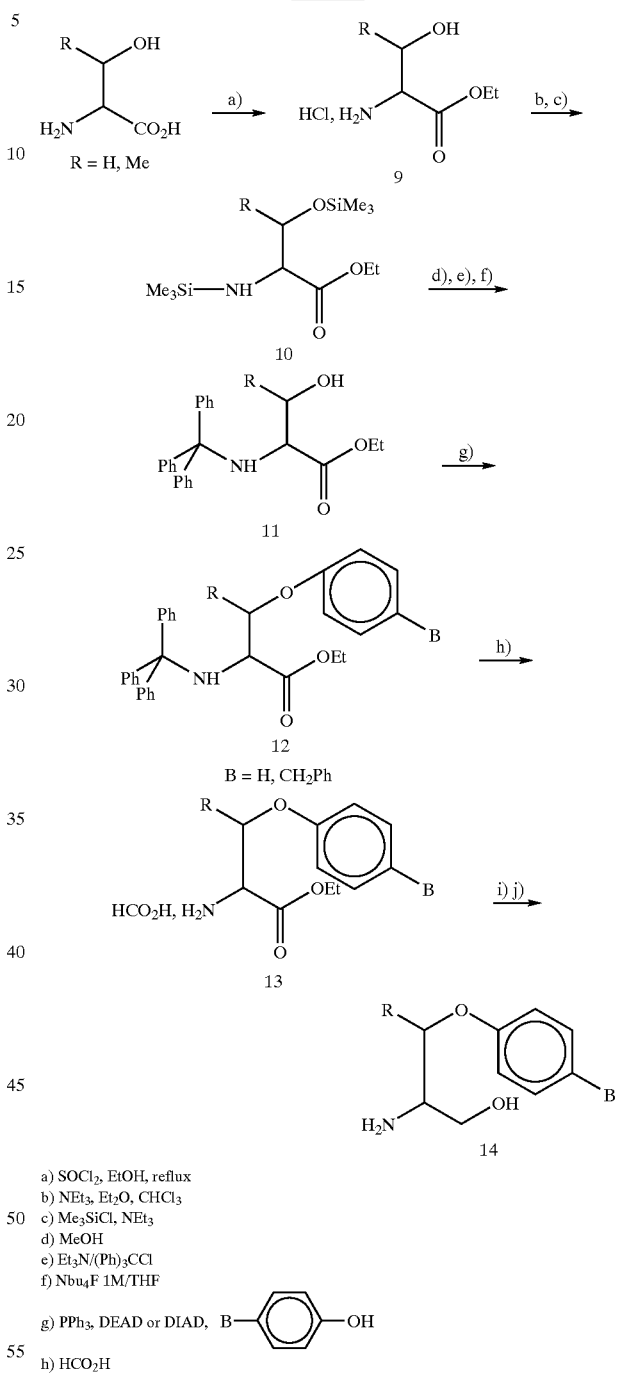

a) SOCl₂, EtOH, reflux
b) NEt₃, Et₂O, CHCl₃
c) Me₃SiCl, NEt₃
d) MeOH
e) Et₃N/(Ph)₃CCl
f) Nbu₄F 1M/THF g) PPh₃, DEAD or DIAD, B—⟨⟩—OH h) HCO₂H
i) NaHCO₃ aq.
j) LAH, Et₂O The serine or the threonine is esterified in the presence of thionyl chloride and EtOH. The amino ester hydrochloride 9 obtained is treated with triethylamine and then with trimethylsilyl chloride in the presence of NEt₃ to give the compound 10. The amino functional group is deprotected using anhydrous MeOH and then reprotected by reacting with trityl chloride. The hydroxyl functional group is then released using tetrabutylammonium fluoride to give the compound 11. The hydroxyl functional group of compound 11 is substituted by a Mitsunobu-type reaction with a phenolic derivative of formula

to give the compound 12. The compounds 14 are obtained by deprotection with formic acid followed by reduction using lithium aluminium hydride.

Scheme 4 describes a method for preparing compounds 17 corresponding to formula (I).

Scheme 4

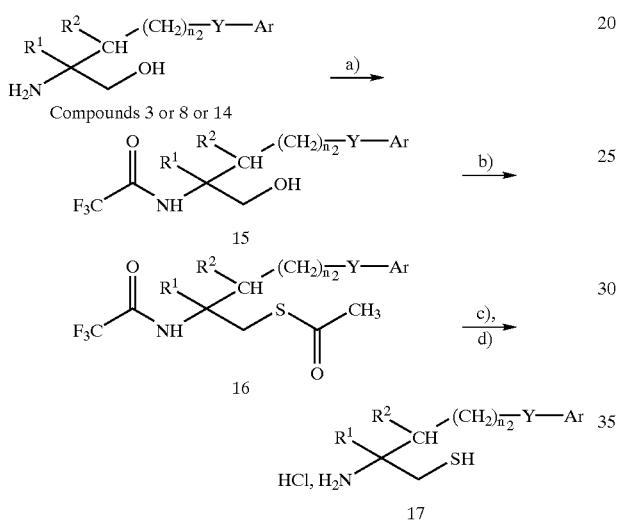

a) trifluoroacetylimidazole, pyridine, 0° C.
b) PPh$_3$, DEAD or DIAD, CH$_3$COSH, THF
c) NaOH, EtOH, H$_2$O, 50° C.
d) HCl 3N The amino functional group of compounds 3, 8 or 14 is protected using trifluoroacetylimidazole in pyridine at 0° C. A Mitsunobu-type reaction is then carried out on compounds 15 in the presence of PPh$_3$, DEAD (or DIAD) and thioacetic acid to give compounds 16. Finally, compounds 17 are obtained by deprotection at 50° C. in a basic medium under an inert atmosphere followed by acidification with an aqueous hydrochloric acid solution.

For the synthesis of compounds 30 of formula (I), a method via mercapto acid derivatives 28 may be used.

These mercapto acid derivatives 28 are prepared from monosubstituted malonates 23 obtained either from commercial halides, or from halides 18, or from activated alcohols 22 (mesylate, tosylate and the like).

Schemes 5 and 6 describe the preparation of noncommercial halides 18 and activated alcohols 22.

Scheme 5

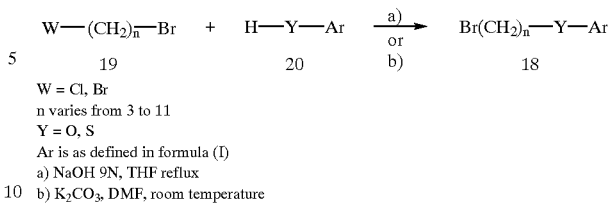

W = Cl, Br
n varies from 3 to 11
Y = O, S
Ar is as defined in formula (I)
a) NaOH 9N, THF reflux
b) K$_2$CO$_3$, DMF, room temperature Compounds 18 may be obtained by two routes: by treatment in 9 N sodium hydroxide under reflux in the presence of THF or by using powdered K$_2$CO$_3$ in DMF at room temperature.

Scheme 6

For the synthesis of the activated alcohols 22 of formula R$^2$—CH(OZ)—(CH$_2$)n$_2$—Y—Ar (Z=Ms, Ts) in which R$^2$, n$_2$, Y and Ar have the definitions cited above in formula (I), the following method is used:

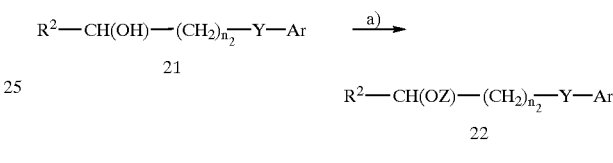

Z = Ms, Ts
a) MsCl or TsCl, CH$_2$Cl$_2$, room temperature.

Scheme 7 describes the synthesis of the monosubstituted malonates 23 obtained by reacting a commercial halide, a halide 18 or an activated alcohol 22 with diethyl malonate.

Scheme 7

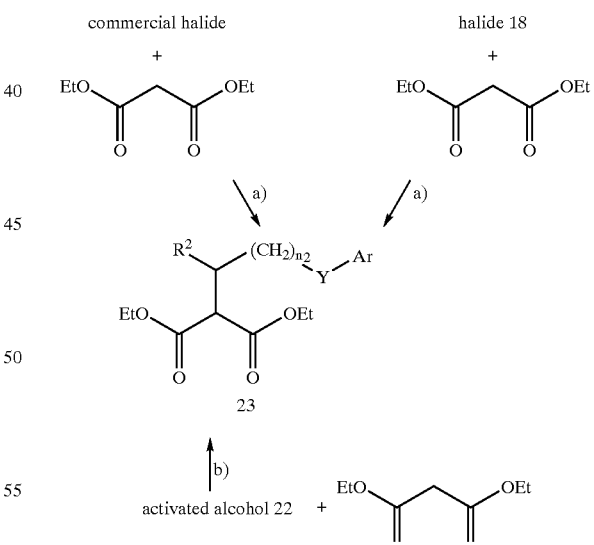

R$^2$, n$_2$, Y and Ar have the definitions mentioned above in formula (I).
a) NaOEt 1.7 M in EtOH, reflux
b) CsF, DMF, 60° C.

The malonates 23 are obtained either from commercial halides, or from the halides 18 by reacting a diethyl malonate in the presence of sodium ethoxide in ethanol under reflux or from the activated alcohols 22 by reacting diethyl malonate in the presence of cesium fluoride in DMF at 60° C.

The malonates 23 are converted to mercapto acid derivatives 28 according to scheme 8.

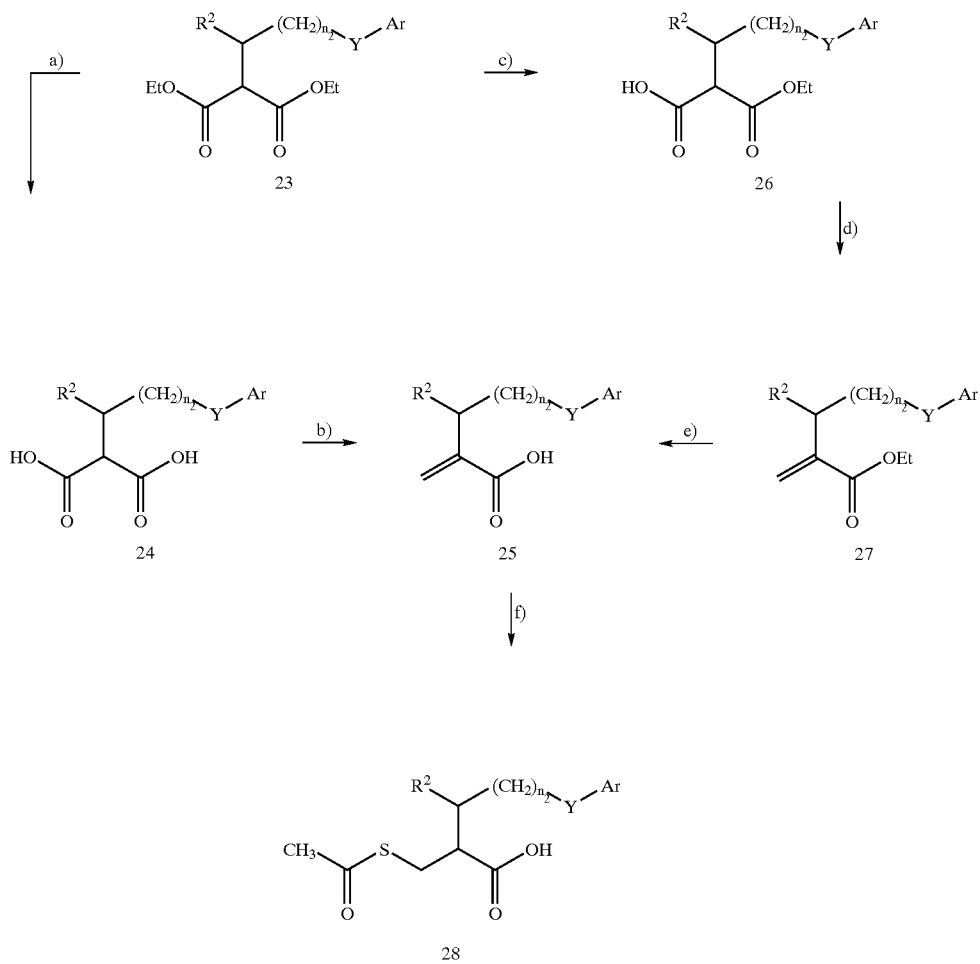

Scheme 8

$R^2$, $n_2$, Y and Ar have the definitions mentioned above in formula (I)
a) NaOH 6 N, reflux
b) paraformaldehyde, HNEt$_2$, AcOEt
c) KOH, EtOH 0° C.
d) formalin 37%, HNEt$_2$
e) NaOH 2 N, acetone, H$_2$O
f) CH$_3$COSH, 70° C.

The acrylic acids 25 are obtained by two routes:
- a two-stage route via the diacids 24 obtained by saponification in 6 N sodium hydroxide under reflux, and then a Mannich reaction in the presence of paraformaldehyde, diethylamine in ethyl acetate under reflux;
- a three-stage route via a monoacid 26 obtained by monosaponification in ethanolic potassium hydroxide at 0° C. followed by a Mannich reaction giving the acrylic esters 27 and then a saponification with 2 N sodium hydroxide in an acetone-water mixture.

The derivatives 28 are obtained by Michael addition of thioacetic acid to the acrylic acids 25 at 70° C.

The derivatives 28 are converted to mercaptoamine derivatives 30 according to scheme 9.

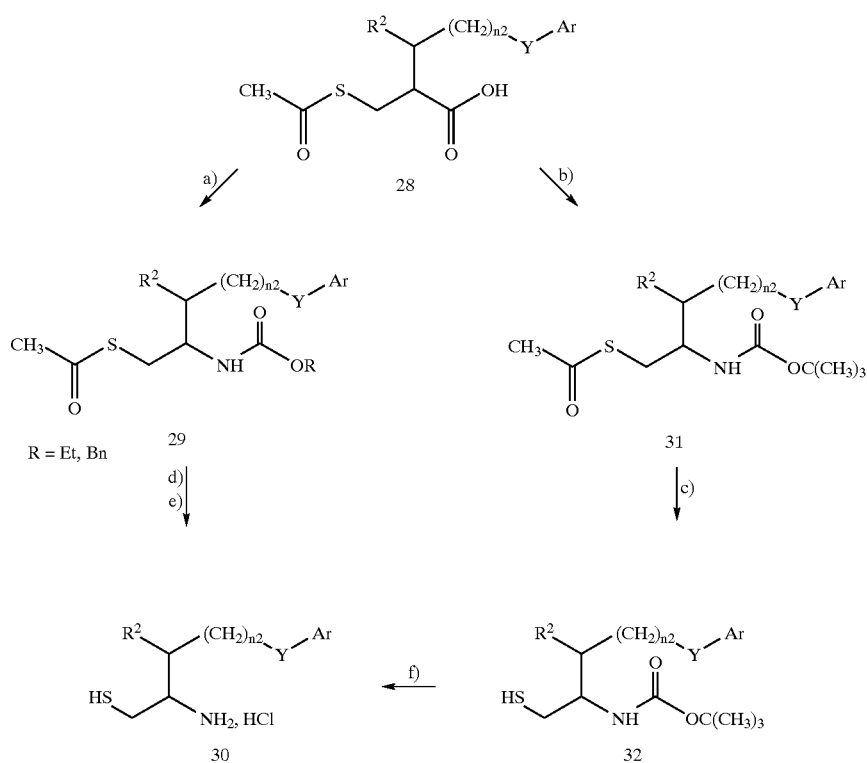

Scheme 9 a) DPPA, Net₃, toluene, ROH, 80° C.
  R = Et, Bn
b) DPPA, Net₃, tBuOH, reflux
c) NaOH 2 N, MeOH, inert atmosphere
d) NaOH 10 N, EtOH, reflux, inert atmosphere
e) HCl 3 N
f) HCl gas, MeOH, -10° C.

The aminothiols of formula 30 are obtained according to two routes:

- a two-stage route which consists in carrying out a Curtius reaction on the acids 28 using DPPA, NEt₃ in toluene and an alcohol such as ethanol or benzyl alcohol at 80° C. overnight. The carbonates 29 are then deprotected with a 10 N solution of sodium hydroxide in the presence of ethanol, under reflux for 2 hours under an inert atmosphere. After acidification with 3 N HCl, the aminothiols 30 are obtained;

- a three-stage route where the Curtius reaction is carried out in tBuOH under reflux to give tert-butyl carbamate 31. The thioester functional group is then saponified with an aqueous solution of sodium hydroxide in the presence of MeOH to give the derivatives 32. The tert-butoxycarbonyl group is then deprotected with a solution of gaseous HCl in MeOH at -10° C. The aminothiols 30 are thus obtained.

Scheme 10

Scheme 10 shows the preparation of disulphides 34 corresponding to the formula (I) from the carbonates 31 described in scheme 9.

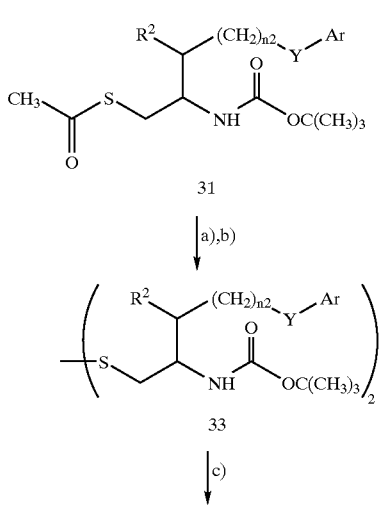

-continued

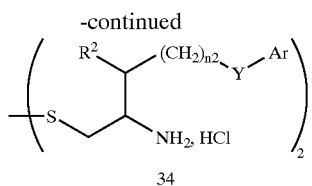

34

R², n₂, Y and Ar have the definitions mentioned above in formula (I)
a) NaOH N, EtOH
b) I₂, EtOH
c) HCl gas, MeOH, -10° C.

The carbamates 31 are subjected to the action of N sodium hydroxide in ethanol and then to the action of a 0.3 M solution of iodine in ethanol to give the N-protected disulphides 33. The tert-butoxycarbonyl group is then deprotected with a gaseous HCl solution in MeOH at −10° C. and the disulphides 34 are thus obtained.

Scheme 11

Scheme 11 shows the preparation of the
S-acetylated compounds 35 corresponding to formula (I)
from the carbamates 29 described in scheme 9.

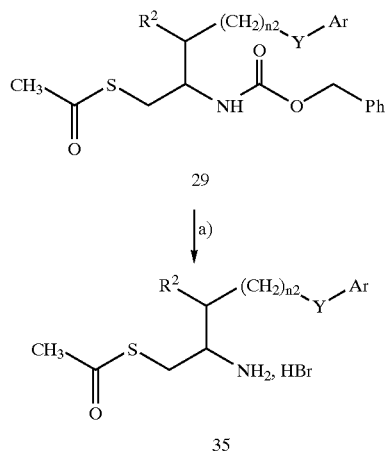

R², n₂, Y and Ar have the definitions mentioned above in formula (I)
a) HBr 30%/AcOH The benzyloxycarbonyl group is deprotected with a 30% gaseous HBr solution in acetic acid at room temperature to give the derivatives 35.

The inventors have also shown that the compounds (I) according to the invention have $LTA_4$ hydrolase inhibiting properties.

They possess an advantageous therapeutic activity, in particular in the field of anti-inflammatory treatments.

They also possess an advantageous antiarthritic activity.

The compounds of the invention also have antipsoriatic properties.

Moreover, the inventors have shown that the compounds of the invention prevent the increase in the tissue levels of $LTB_4$ which is induced by cyclooxygenase inhibitors.

They are thus useful for the prevention of certain paradoxical pro-inflammatory side effects of cyclooxygenase inhibitors.

Finally, $LTB_4$ being the endogenous ligand for the receptor inducing proliferation of the peroxisomes, the compounds of the invention also find application in the fields of hepatoprotection and antimitotic action.

The subject of the present invention is thus also the use of the compounds of formula (I) as medicaments which act as inhibitors of the activity of $LTA_4$ hydrolase, in particular for an anti-inflammatory or antiarthritic treatment.

Its subject is also the use of the compounds of the invention as antipsoriatic medicaments.

Its subject is also their use as hepatoprotective or antimitotic medicaments.

Its subject is also the use of such compounds as medicaments intended for the treatment of an overproduction of $LTB^4$, induced in particular by cyclooxygenase inhibitors.

Its subject is also the use of such compounds (I) for the preparation of medicaments intended for inhibiting the activity of $LTA_4$ hydrolase.

Its subject is in particular their use for the preparation of medicaments intended for the abovementioned treatments.

The compounds of formula (I) may be administered in a physiologically acceptable vehicle or excipient.

Accordingly, the subject of the present invention is also pharmaceutical compositions comprising a therapeutically effective quantity of at least one compound of formula (I) in combination with a physiologically acceptable vehicle or excipient.

The compounds (I) of the invention may also be used in combination with cyclooxygenase inhibitors.

The invention thus relates to medicaments or pharmaceutical compositions containing a therapeutically effective quantity of a compound (I) and a therapeutically effective quantity of a cyclooxygenase inhibiting compound, optionally in combination with a physiologically acceptable vehicle or excipient.

Examples of cyclooxygenase inhibitors useful according to the invention are aspirin (acetylsalicylic acid), ibuprofen and dichlofenac.

The medicaments or pharmaceutical compositions according to the invention may be advantageously administered by the local cutaneous or ocular routes, by the parenteral route or by the oral route, the latter being preferred.

The subject of the invention is also a method of treatment for inhibiting the activity of $LTA_4$ hydrolase in humans.

Its subject is also such a method for the treatments indicated above.

Its subject is also a method of treating an overproduction of $LTB_4$, in particular induced by cyclooxygenase inhibitors.

Other advantageous characteristics of the present invention will emerge on reading the examples of preparation of compounds of formula (I) given by way of nonlimiting illustration, as well as the biological results given below.

EXAMPLES

A summary table of the examples of compounds of formula (I) is given below:

Summary table of the examples of compounds of formula (I)
| Ex | Configuration | X | R¹ | $n_1$ | R² | $n_2$ | Y | Ar | R³ |
|---|---|---|---|---|---|---|---|---|---|
| 22 | (S) | —NH$_2$ | —H | 1 | —H | 0 | —O— | —Ph | —H |
| 23 | (S) | —NH$_2$ | —H | 1 | —H | 0 | —SCH$_2$— | —Ph | —H |
| 24 | (S) | —NH$_2$ | —H | 1 | —H | 0 | —OCH$_2$— | —Ph | —H |
| 25 | (R) | —NH$_2$ | —H | 1 | —H | 0 | —OCH$_2$— | —Ph | —H |
| 26 | (2S,3R) | —NH$_2$ | —H | 1 | —CH$_3$ | 0 | —OCH$_2$— | —Ph | —H |
| 27 | (2R,3S) | —NH$_2$ | —H | 1 | —CH$_3$ | 0 | —OCH$_2$— | —Ph | —H |
| 28 | (RS) | —NH$_2$ | —H | 1 | —H | 3 | —CH$_2$— | —Ph | —H |
| 29 | (RS) | —NH$_2$ | —CH$_3$ | 1 | —H | 3 | —O— | 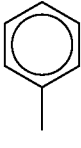 | —H |
| 30 | (S) | —NH$_2$ | —H | 1 | —H | 0 | —O— | 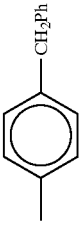 | —H |
| 155 | (RS) | —NH$_2$ | —H | 1 | —H | 0 | —CH$_2$— | —Ph | —H |
| 156 | (RS) | —NH$_2$ | —H | 1 | —H | 3 | —O— | —Ph | —H |
| 157 | (RS) | —NH$_2$ | —H | 1 | —H | 4 | —O— | —Ph | —H |
| 158 | (RS) | —NH$_2$ | —H | 1 | —H | 4 | —O— |  | —H |
| 159 | (RS) | —NH$_2$ | —H | 1 | —H | 3 | —O— | 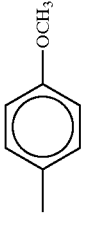 | —H |

-continued

Summary table of the examples of compounds of formula (I)

| Ex | Configuration | X | R¹ | n₁ | R² | n₂ | Y | Ar | R³ |
|---|---|---|---|---|---|---|---|---|---|
| 160 | (RS) | —NH₂ | —H | 1 | —H | 3 | —O— | 4-CH₃-C₆H₄ | —H |
| 161 | (RS) | —NH₂ | —H | 1 | —H | 3 | —O— | 3-CH₃-C₆H₄ | —H |
| 162 | (RS) | —NH₂ | —H | 1 | —H | 3 | —O— | 3-OCH₃-C₆H₄ | —H |
| 163 | (RS) | —NH₂ | —H | 1 | —H | 3 | —O— | 4-Cl-C₆H₄ | —H |
| 164 | (RS) | —NH₂ | —H | 1 | —H | 3 | —O— | 4-Br-C₆H₄ | —H |
| 165 | (RS) | —NH₂ | —H | 1 | —H | 3 | —O— | 4-F-C₆H₄ | —H |
| 166 | (RS) | —NH₂ | —H | 1 | —H | 3 | —O— | 2-OCH₃-C₆H₄ | —H |

Summary table of the examples of compounds of formula (I)
| Ex | Configuration | X | R¹ | n₁ | R² | n₂ | Y | Ar | R³ |
|---|---|---|---|---|---|---|---|---|---|
| 167 | (RS) | —NH₂ | —H | 1 | —H | 3 | —S— | —Ph | —H |
| 168 | (RS) | —NH₂ | —H | 1 | —H | 3 | —O— | 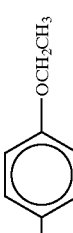 | —H |
| 169 | (RS) | —NH₂ | —H | 1 | —H | 3 | —O— | 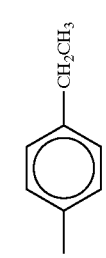 (4-OCH₂CH₃-phenyl) | —H |
| 170 | (RS) | —NH₂ | —H | 1 | —H | 3 | —O— |  (4-CH₂CH₃-phenyl) | —H |
| 171 | (RS) | —NH₂ | —H | 1 | —H | 1 | —CH₂— | —Ph | —H |
| 172 | (RS) | —NH₂ | —H | 1 | —H | 1 | —O— | —Ph | —H |
| 173 | (RS) | —NH₂ | —H | 1 | —H | 2 | —CH₂— | —Ph | —H |
| 174 | (RS) | —NH₂ | —H | 1 | —H | 1 | —S— | —Ph | —H |
| 175 | (RS) | —NH₂ | —H | 1 | —H | 3 | —O— | 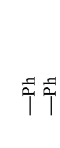 (2,6-diCH₃-phenyl) | —H |
| 176 | (RS) | —NH₂ | —H | 1 | —H | 1 | —SCH₂— | —Ph | —H |
| 177 | (RS) | —NH₂ | —H | 1 | —H | 2 | —O— | —Ph | —H |
| 178 | (RS) | —NH₂ | —H | 1 | —H | 3 | —O— |  (2-CH₃-phenyl) | —H |
| 179 | (RS) | —NH₂ | —H | 1 | —H | 3 | —O— | 4-OPh-phenyl | —H |

-continued

Summary table of the examples of compounds of formula (I)

| Ex | Configuration | X | R¹ | n₁ | R² | n₂ | Y | Ar | R³ |
|---|---|---|---|---|---|---|---|---|---|
| 180 | (RS) | —NH₂ | —H | 1 | —H | 3 | —O— | 4-COOH-C₆H₄— | —H |
| 183 | (RS) | —NH₂ | —H | 1 | —H | 3 | —O— | 4-CN-C₆H₄— | —H |
| 184 | (RS) | —NH₂ | —H | 1 | —CH₃ | 3 | —O— | —Ph | —H |
| 185 | (RS) | —NH₂ | —H | 1 | —H | 3 | —O— | 4-Ph-C₆H₄— | —H |
| 186 | (RS) | —NH₂ | —H | 1 | —H | 3 | —O— | 4-OCH₂Ph-C₆H₄— | —H |
| 187 | (RS) | —NH₂ | —H | 1 | —H | 3 | —O— | 2-naphthyl | —H |
| 188 | (RS) | —NH₂ | —H | 1 | —H | 3 | —O— | 1-naphthyl | —H |
| 189 | (RS) | —NH₂ | —H | 1 | —H | 3 | —O— | —Ph | —H |
| 190 | (RS) | —NH₂ | —H | 1 | —H | 3 | —O— | —Ph | —H |
| 191 | (RS) | —NH₂ | —H | 1 | —H | 3 | —O— | 3-CF₃-C₆H₄— | —H |

-continued
Summary table of the examples of compounds of formula (I)
| Ex | Configuration | X | R¹ | n₁ | R² | n₂ | Y | Ar | R³ |
|---|---|---|---|---|---|---|---|---|---|
| 192 | (RS) | —NH₂ | —H | 1 | —H | 3 | —O— |  | —H |
| 193 | (RS) | —NH₂ | —H | 1 | —H | 3 | —O— |  | —H |
| 194 | (RS) | —NH₂ | —H | 1 | —H | 3 | —O— |  | —H |
| 195 | (RS) | —NH₂ | —H | 1 | —H | 3 | —O— |  | —H |
| 196 | (RS) | —NH₂ | —H | 1 | —H | 3 | —O— |  | —H |
| 197 | (RS) | —NH₂ | —H | 1 | —H | 4 | —CH₂— | —Ph | —H |
| 198 | (RS) | —NH₂ | —H | 1 | —H | 3 | —O— |  | —H |

Summary table of the examples of compounds of formula (I) -continued
| Ex | Configuration | X | R¹ | n₁ | R² | n₂ | Y | Ar | R³ |
|---|---|---|---|---|---|---|---|---|---|
| 199 | (RS) | —NH₂ | —H | 1 | —H | 3 | —O— |  4-O(CH₂)₃CH₃-phenyl | —H |
| 200 | (RS) | —NH₂ | —H | 1 | —H | 3 | —O— |  3,4-dichlorophenyl | —H |
| 201 | (RS) | —NH₂ | —H | 1 | —H | 3 | —O— |  2-pyridyl | —H |
| 202 | (RS) | —NH₂ | —H | 1 | —H | 3 | —O— |  3-CN-phenyl | —H |
| 203 | (RS) | —NH₂ | —H | 1 | —H | 2 | —O— |  4-CH₂Ph-phenyl | —H |
| 204 | (RS) | —NH₂ | —H | 1 | —H | 3 | —O— |  3-Cl-phenyl | —H |
| 205 | (RS) | —NH₂ | —H | 1 | —H | 4 | —O— |  4-CN-phenyl | —H |
| 206 | (RS) | —NH₂ | —H | 1 | —H | 2 | —O— |  4-CN-phenyl | —H |

-continued

Summary table of the examples of compounds of formula (I)

| Ex | Configuration | X | R¹ | $n_1$ | R² | $n_2$ | Y | Ar | R³ |
|---|---|---|---|---|---|---|---|---|---|
| 207 | (RS) | —NH₂ | —H | 1 | —H | 3 | —O— | 3-CH₂CH₃, 5-CH₃ phenyl | —H |
| 208 | (RS) | —NH₂ | —H | 1 | —H | 3 | —O— | 4-CF₃, 4-CH₃ phenyl | —H |
| 209 | (RS) | —NH₂ | —H | 1 | —H | 4 | —O— | 4-CH₂Ph phenyl | —H |
| 210 | (RS) | —NH₂ | —H | 1 | —H | 3 | —O— | 4-CH₂Ph phenyl | —H |
| 211 | (RS) | —NH₂ | —H | 1 | —H | 2 | —O— | 3-CH₂CH₃, 5-CH₃ phenyl | —H |
| 212 | (RS) | —NH₂ | —H | 1 | —H | 2 | —O— | 4-CH₃ phenyl | —H |
| 213 | (RS) | —NH₂ | —H | 1 | —H | 3 | —O— | 4-CH₃, NHC(O)CH₃ phenyl | —H |
| 214 | (RS) | —NH₂ | —H | 1 | —H | 3 | —O— | 4-I phenyl | —H |

-continued

Summary table of the examples of compounds of formula (I)

| Ex | Configuration | X | $R^1$ | $n_1$ | $R^2$ | $n_2$ | Y | Ar | $R^3$ |
|---|---|---|---|---|---|---|---|---|---|
| 215 | (RS) | —NH$_2$ | —H | 1 | —H | 3 | —O— |  4-O(CH$_2$)$_2$CH$_3$-C$_6$H$_4$— | —H |
| 216 | (RS) | —NH$_2$ | —H | 1 | —H | 2 | —O— |  4-(C(O)Ph)-C$_6$H$_4$— | —H |
| 217 | (RS) | —NH$_2$ | —H | 1 | —H | 2 | —O— |  4-OC$_2$H$_5$-C$_6$H$_4$— | —H |
| 218 | (RS) | —NH$_2$ | —H | 1 | —H | 4 | —O— |  4-OC$_2$H$_5$-C$_6$H$_4$— | —H |
| 223 | (+) | —NH$_2$ | —H | 1 | —H | 3 | —O— |  4-OC$_2$H$_5$-C$_6$H$_4$— | —H |
| 224 | (−) | —NH$_2$ | —H | 1 | —H | 3 | —O— |  4-OC$_2$H$_5$-C$_6$H$_4$— | —H |
| 225<br>226 | (+)<br>(−) | —NH$_2$<br>—NH$_2$ | —H<br>—H | 1<br>1 | —H<br>—H | 3<br>3 | —O—<br>—O— | —Ph<br>—Ph | —H<br>—H |
| 229 | (RS, RS) | —NH$_2$ | —H | 1 | —H | 3 | —O— | —Ph |  —CH$_2$CH(NH$_2$)CH$_2$SCH$_2$(CH$_2$)$_3$—O—Ph |
| 230<br>231 | (+) isomer A<br>(−) isomer B | —NH$_2$ | —H | 1 | —H | 3 | —O— | —Ph | —CH$_2$CH(NH$_2$)CH$_2$S(CH$_2$)$_4$(CH$_2$)$_3$—OPh |

-continued

Summary table of the examples of compounds of formula (I)

| Ex | Configuration | X | $R^1$ | $n_1$ | $R^2$ | $n_2$ | Y | Ar | $R^3$ |
|---|---|---|---|---|---|---|---|---|---|
| 232<br>233<br>234 | (RS, RS)<br>(+) isomer A<br>(−) isomer B | —NH$_2$ | —H | 1 | —H | 3 | —O— | 4-ethoxyphenyl (p-OEt-C$_6$H$_4$—) | —(CH$_2$)$_4$—CH(NH$_2$)—CH$_2$—S—(CH$_2$)$_3$—O—C$_6$H$_4$-OEt |
| 235 | (RS, RS) | —NH$_2$ | —H | 1 | —H | 3 | —O— | 4-(NHCOCH$_3$)-C$_6$H$_4$— | —(CH$_2$)$_4$—CH(NH$_2$)—CH$_2$—S—(CH$_2$)$_3$—O—C$_6$H$_4$—NHCOCH$_3$ |
| 236 | (RS, RS) | —NH$_2$ | —H | 1 | —H | 3 | —O— | 4-CN-C$_6$H$_4$— | —(CH$_2$)$_4$—CH(NH$_2$)—CH$_2$—S—(CH$_2$)$_3$—O—C$_6$H$_4$-CN |
| 238 | (RS) | —NH$_2$ | —H | 1 | —H | 3 | —O— | —Ph | —C(=O)—CH$_3$ |

In the examples given below, the following abbreviations have been used for the NMR data: s=singlet, d=doublet, t=triplet, q=quadruplet, m=multiplet.

Example 1

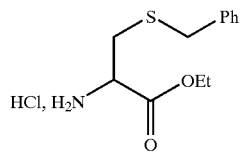

4.7 g of thionyl chloride are added to a suspension of 5 g (23.6 mmol) of (S)-benzyl-L-cysteine in 50 ml of EtOH cooled to 0° C.

The medium is then heated under reflux for 3 hours, concentrated in a rotary evaporator and the residue taken up in 50 ml of Et$_2$O.

The medium is filtered, the precipitate is washed with Et$_2$O and dried under vacuum. 6.37 g of a white solid are obtained (98%).

The $^1$H NMR at 200 MHz is in agreement with the structure.

Example 2

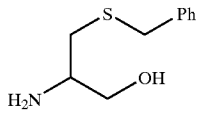

A solution of 2.45 g (24.2 mmol) of NEt$_3$ in 75 ml of Et$_2$O is added at 0° C. to a suspension of 5.6 g (20.25 mmol) of the product of Example 1. The medium is stirred for 2 hours at 0° C., filtered and the filtrate is evaporated to dryness. 2.7 g (11.3 mmol) of free amino ester are obtained, which ester is taken up in 7 ml of anhydrous Et$_2$O and which is added at 0° C. to a suspension of 0.52 g (13.7 mmol) of LAH in 36 ml of anhydrous Et$_2$O. The medium is stirred overnight at room temperature and then hydrolysed successively with 0.5 ml of water, 0.5 ml of 15% sodium hydroxide and 1.5 ml of water.

The medium is stirred for 2 hours at room temperature, filtered, the precipitate rinsed with Et$_2$O and the filtrate is concentrated under vacuum. 1.64 g (8.3 mmol) of an oily amino alcohol are thus obtained.

Examples 3 to 6 are prepared according to the same reaction sequence.

TABLE 1

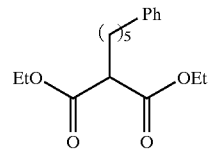

| Ex. No. | Product | Absolute configuration* |
|---|---|---|
| 3 | H$_2$N—CH(CH$_2$OCH$_2$Ph)—CH$_2$OH | (S) |
| 4 | H$_2$N—CH(CH$_2$OCH$_2$Ph)—CH$_2$OH | (R) |
| 5 | CH$_3$—(R)CH(OCH$_2$Ph)—CH(NH$_2$)—CH$_2$OH | (S) |
| 6 | CH$_3$—(S)CH(OCH$_2$Ph)—CH(NH$_2$)—CH$_2$OH | (R) |

Example 7

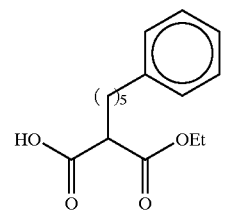

A solution of sodium ethoxide, prepared from 12 g (300 mmol) of sodium in 306 ml of EtOH, is added to a mixture of 141 g (881.15 mmol) of diethyl malonate and 38.4 g (210 mmol) of 5-phenyl-1-chloropentane. The medium is heated under reflux for 4 hours.

The medium is concentrated under vacuum, the residue taken up in water and extracted with Et$_2$O.

The ethereal phase is washed 3 times with water, dried over MgSO$_4$, filtered and then concentrated. The excess diethyl malonate is removed by distillation under vacuum.

57.2 g (yield 89%) of yellow oil are obtained.

Example 8

A solution of 2.7 g (40.9 mmol) of potassium hydroxide in 58 ml of EtOH is added at 0° C. to a solution of 12.25 g (40 mmol) of the diester of Example 7 in 21 ml of EtOH.

The medium is stirred overnight at 0° C.

The medium is then concentrated. The residue is taken up in 100 ml of water and washed with Et₂O (twice 30 ml). The aqueous phase is cooled and then acidified with a concentrated hydrochloric acid solution. The aqueous phase is extracted with ether (twice 40 ml). The ethereal phases are combined, dried over MgSO₄, filtered and concentrated. 9.8 g (yield 88%) of a very viscous yellow oil are thus obtained.

Example 9

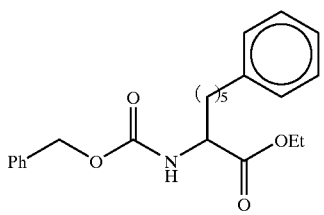

10.34 g (37.53 mmol) of DPPA and then 3.77 g (37.32 mmol) of NEt₃ are added dropwise to a solution of 9.8 g of the monoacid of Example 8 in 36 ml of toluene. The medium is heated at 80° C. for 1 hour. The medium is allowed to return to room temperature and 4.75 g (43.98 mmol) of benzyl alcohol are added and the medium is heated at 80° C. overnight. The toluene phase is successively washed with water (once 10 ml), with a saturated aqueous sodium hydrogen carbonate solution (once 10 ml) and with water (once 5 ml). The organic phase is dried over MgSO₄, filtered and concentrated under vacuum.

13.1 g of crude product are thus obtained.

The latter is purified by flash chromatography on silica with the ethyl ether—petroleum ether (3/7) mixture as eluent. 8.1 g of carbamate are obtained (21 mmol; yield= 61%).

Example 10

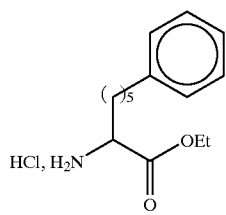

8.1 g (21 mmol) of the carbamate of Example 9 are dissolved in 60 ml of EtOH. 200 mg of 10% Pd/C are then added and then the medium is hydrogenated at a pressure of about 1 bar overnight at room temperature. The suspension is filtered on celite and then evaporated to dryness. The oily residue is taken up in a concentrated aqueous HCl solution. The acidic aqueous phase is washed with Et₂O (twice 20 ml). The aqueous phase is evaporated to dryness and the residue is dried under vacuum on P₂O₅ to a constant mass. 5.4 g (yield 90%) of a white solid are thus obtained.

Example 11

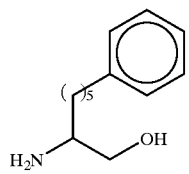

The product of Example 10 is reduced to an amino alcohol 11 according to the method described in Example 2. Yield= 84%.

Example 12

Example 12 is prepared according to the same reaction sequence as that described in Example 11.

TABLE 2

| Ex. No. | Starting material | Amino alcohol prepared |
|---|---|---|
| 12 | PhO~(CH₂)₄~Br | H₃C–C(NH₂)(CH₂)₄OPh–CH₂OH | ex. 31

Example 13

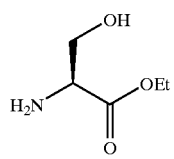

A solution of 16.9 g (100 mmol) of ethyl serinate hydrochloride obtained according to the method described in Example 1, but starting with serine, in 150 ml of chloroform, is cooled to 0–5° C. 500 ml of Et₂O and 10.12 g (100 mmol) of triethylamine are added.

The medium is stirred for 2 hours at 0° C. It is filtered and evaporated to dryness.

11.98 g of a colourless oil (90%) are obtained.

Example 14

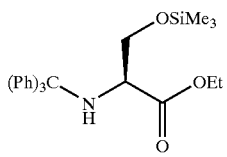

The 11.98 g (90 mmol) of the product of Example 13 are dissolved in 155 ml of $CH_2Cl_2$. 22.78 g (209.68 mmol) of trimethylsilyl chloride are added under an inert atmosphere.

The medium is heated under reflux for 20 minutes and then allowed to return to room temperature. 21.2 g (209.90 mmol) of triethylamine in 60 ml of $CH_2Cl_2$ are then added and then the medium is heated under reflux for 45 minutes.

The medium is then cooled to 0° C. and a solution of 5.4 ml (135 mmol) of anhydrous methanol in 22 ml of $CH_2Cl_2$ is added. The temperature of the medium is allowed to rise to room temperature and then 9.1 g (90 mmol) of $NEt_3$ and 25 g (90 mmol) of trityl chloride are successively added and the medium is stirred overnight at room temperature.

The medium is concentrated under vacuum and taken up in 200 ml of $Et_2O$. The medium is washed with water (once 30 ml).

The medium is dried over $MgSO_4$, filtered and concentrated under vacuum.

38.8 g of the desired compound are obtained.

Example 15

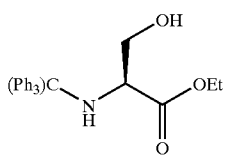

50 ml of a molar solution of tetrabutylammonium fluoride ($Nbu_4F$) in THF are added at room temperature to a solution of 38.8 g of the product of Example 14 in 53 ml of THF. The medium is stirred for 10 minutes at room temperature.

500 ml of $Et_2O$ are then added and the organic phase is successively washed with a saturated aqueous hydrogen carbonate solution (twice 60 ml) and then a saturated aqueous sodium thiosulphate solution (twice 60 ml). The organic phase is dried over $MgSO_4$, filtered and concentrated under vacuum. The oily residue obtained is purified by flash chromatography using the petroleum ether/$Et_2O$ (1/1) mixture and then $Et_2O$ as eluents.

29.31 g (78 mmol) of the desired compound are obtained.

Example 16

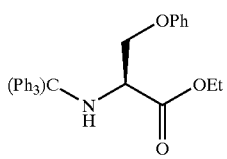

14.75 g (56.23 mmol) of triphenylphosphine and 7.2 g (76.5 mmol) of phenol are successively added to a solution of 19.85 g (52.59 mmol) of the amino ester of Example 15 in 300 ml of toluene. The reaction medium is vigorously stirred for 5 minutes, and then 11.37 g (56.2 mmol) of diisopropyl azodicarboxylate are added.

The reaction medium is stirred overnight at room temperature, filtered and evaporated to dryness. The oily residue is purified by flash chromatography using the ether-petroleum ether (5/95) mixture as eluent. 15.43 g (34 mmol) of the desired compound are thus obtained.

Example 17

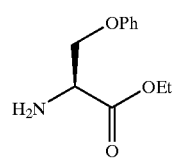

7.6 g (16.7 mmol) of the amino ester of Example 16 are vigorously stirred for 5 hours at room temperature in the presence of 104 ml of formic acid. The reaction medium is then evaporated to dryness and a white solid is obtained which is taken up in 100 ml of water. The aqueous phase is washed with $Et_2O$ (3 times 20 ml) and is then basified with sodium hydrogen carbonate. The basic aqueous phase is then extracted with ethyl acetate (3 times 20 ml). The organic phase is dried over $MgSO_4$, filtered and concentrated under vacuum. 2.1 g (10.1 mmol) of the desired compound are obtained.

Example 18

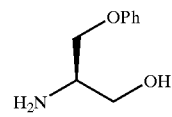

The 2.1 g (10.1 mmol) of amino ester of Example 17 are taken up in 4 ml of anhydrous $Et_2O$ and added at 0° C. to a suspension of 0.46 g (12.1 mmol) of LAH in 30 ml of anhydrous $Et_2O$. The medium is stirred overnight at room temperature and then successively hydrolysed with 0.3 ml of water, 0.3 ml of 15% sodium hydroxide and 0.9 ml of water. The medium is stirred for 2 hours at room temperature, filtered, the precipitate rinsed with $Et_2O$ and the filtrate concentrated under vacuum. 1.35 g (8.1 mmol) of an oily amino alcohol are thus obtained.

Example 19

Example 19 is prepared according to the same reaction sequence as that described in Example 18.

TABLE 3

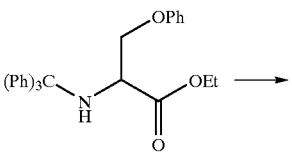

| Ex. No. | Starting phenol | Amino alcohol prepared |
|---|---|---|
| 19 |  |  |

Example 20

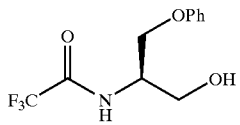

2.6 g (15.85 mmol) of trifluoroacetylimidazole are added at 0° C. to a solution of 2.65 g (15.85 mmol) of the amino alcohol 18 in 10 ml of pyridine. After stirring for 30 minutes at 0° C., the reaction medium is acidified with 10% aqueous phosphonic acid, and the aqueous phase is extracted with Et$_2$O (twice 15 ml). The combined ethereal phases are washed with 10% H$_3$PO$_4$ (once 10 ml) and then dried over MgSO$_4$. The medium is filtered and concentrated under vacuum. The crude product is purified by flash chromatography using the Et$_2$O/petroleum ether (1/1) mixture as eluent. 2.31 g (8.77 mmol) of the expected product are thus obtained.

Example 21

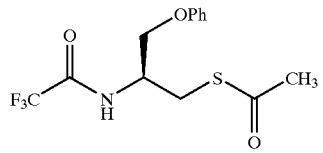

2.3 g (13.2 mmol) of DEAD are added at 0° C. to 3.45 g (13.15 mmol) of triphenylphosphine in solution in 32 ml of THF. The medium is stirred for 30 minutes at 0° C. (appearance of a white precipitate). A solution of 1 g (13.14 mmol) of thioacetic acid and 2.31 g (8.77 mmol) of the alcohol obtained in Example 20 in 16 ml of THF are then added at this temperature. The reaction medium is stirred for 2 hours at 0° C. and then allowed to return to room temperature. After stirring overnight, the medium is evaporated to dryness. The residue is taken up in 100 ml of Et$_2$O and the organic phase is then washed with a saturated aqueous NaHCO$_3$ solution (3 times 15 ml). The ethereal phase is dried over MgSO$_4$, filtered and concentrated under vacuum. The residue is taken up in 60 ml of an AcOEt-petroleum ether (1/1) mixture and stirred for 1 hour at 0° C. The medium is filtered and the filtrate is evaporated under vacuum. 4.92 g of crude product are obtained, which product is purified by flash chromatography using the ether-petroleum ether (2/8) mixture as eluent. 1.6 g (4.95 mmol) of the expected product are thus recovered.

Example 22

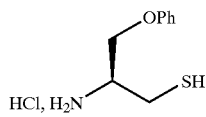

35 ml of a 2 N solution of sodium hydroxide (water-ethanol 1/1) are added under argon to 1.6 g (4.95 mmol) of the product obtained in Example 21. The reaction medium is heated for 2 hours at 50° C., the temperature is allowed to return to room temperature and the EtOH is removed under vacuum. The reaction medium is cooled to 5° C. and acidified under argon with 6 N HCl. The acidic aqueous phase is washed with Et$_2$O (twice 10 ml) and then concentrated under vacuum. The solid residue is extracted with chloroform under reflux. After filtration, the chloroform phases are evaporated to dryness. A white solid is obtained which is purified by trituration in 10 ml of anhydrous Et$_2$O. After filtration, the solid is dried in a desiccator over P$_2$O$_5$.

0.73 g (3.3 mmol) of aminothiol hydrochloride is obtained.

$^1$H NMR (200 MHz, D$_2$O): 7.35 to 7.15 (m, 2H); 7.0 to 6.8 (m, 3H); 4.60 (s, 4H); 4.3 to 4.0 (m, 2H); 3.75 to 3.55 (m, 1H); 3.0 to 2.7 (m, 2H). m.p.=150° C.

Examples 23 to 30 are prepared from the corresponding amino alcohols according to the same reaction sequence as that described for Example 22:

Example 31

(Method a)

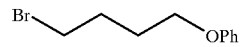

17.41 g (185.25 mmol) of phenol, 14.5 ml of THF and 62 ml of 9 N NaOH are introduced into a round-bottomed flask.

40 g (185.25 mmol) of 1,4-dibromobutane are added dropwise.

The medium is stirred and heated under reflux for 45 minutes.

After cooling, the medium is diluted with 50 ml of water and then extracted with 100 ml of Et$_2$O. The organic phase

TABLE 4

| Ex. No. (conf.) | Compound | Starting material | Analyses |
|---|---|---|---|
| 23 (S) | | Ex. 2 | $^1$H NMR (200MHz, CDCl$_3$): 8.45(m, 3H); 7.4 to 7.1(m, 5H); 3.65(s, 2H); 3.5 to 3.3(m, 1H); 3.05 to 2.65(m, 4H); 0.95(t, 1H, J=7.4Hz) |
| 24 (S) | | Ex. 3 | $^1$H NMR (200MHz, CDCl$_3$): 8.45(m, 3H); 7.4 to 7.15(m, 5H); 4.65 to 4.45(m, 2H); 3.8 to 3.65 (m, 2H); 3.6 to 3.4(m, 1H); 3.05 to 2.7(m, 2H); 1.9(t, 1H, J=7.4Hz) |
| 25 (R) | | Ex. 4 | $^1$H NMR (200MHz, CDCl$_3$): 8.45(m, 3H); 7.4 to 7.15(m, 5H); 4.65 to 4.45(m, 2H); 3.8 to 3.65 (m, 2H ; 3.6 to 3.4(m, 1H); 3.05 to 2.7(m, 2H); 1.9(t, 1H, J=7.4Hz) |
| 26 (2S, 3R) | | Ex. 5 | $^1$H NMR (200MHz, D$_2$O): 7.25(s, 5H); 4.6(s, 4H); 4.55 and 4.35(AB, 2H, X=7.5Hz); 3.8 to 3.6(m, 1H); 3.25 to 3.1(m, 1H); 2.9 to 2.55 (m, 2H); 1.1(d, 3H, J=6.7 Hz). [α]$_D$=−32.7°(c=1.17, MeOH, 26° C.) |
| 27 (2S, 3R) | | Ex. 6 | $^1$H NMR (200MHz, D$_2$O): 7.25(s, 5H); 4.6(s, 4H); 4.55 and 4.35(AB, 2H, X=7.5Hz); 3.8 to 3.6(m, 1H); 3.25 to 3.1(m, 1H); 2.9 to 2.55 (m, 2H); 1.1(d, 3H, J=6.7 Hz). [α]$_D$=+33.2°(c=1.26, MeOH, 26° C.) |
| 28 (RS) | | Ex. 11 | $^1$H NMR (200MHz, CDCl$_3$); 8.4(m, 3H); 7.35 to 7.05 (m, 5H); 3.45 to 3.2(m, 1H); 3.0 to 2.7 (m, 2H); 2.55(t, 2J, J=7.3Hz); 1.95(t, 1H, J=7.4Hz); 1.9 to 1.2(m, 8H)<br>$^{13}$C NMR (50MHz, D$_2$O): 145,6; 131.2; 131.1; 128.4; 55.6; 37.9; 33.4; 30.9; 28.5; 27.1 |
| 29 (RS) | | Ex. 12 | $^1$H NMR (200MHz, CDCl$_3$): 8.45(broad s, 3H); 7.3 to 7.15(m, 3H); 7.0 to 6.75(m, 2H); 3.9(t, 2H, J=6.7Hz); 2.95 to 3.7(m, 2H); 2.0 to 1.65 (m, 5H); 1.65 to 1.3(m, 2H); 1.45(s, 3H) |
| 30 (S) | | Ex. 19 | $^1$H NMR (200MHz, DMSO): 8.6(broad s, 3H); 7.35 to 7.05(m, 2H); 7.0 to 6.8(m, 2H); 4.15(t, 2H, J=6.7Hz); 3.85(s, 2H); 3.6 to 3.4 (m, 1H); 3.15(t, 1H, J=7.4Hz); 3.0 to 2.75(m, 2H) | is washed with 30 ml of water, dried over MgSO$_4$, filtered and concentrated.

The oily residue is distilled using a slide vane rotary vacuum pump.

The fraction which distils at 80°–105° C. at 1 mm of Hg is recovered.

15.96 g (37%) of colourless oil are obtained.

Example 32

(Method b)

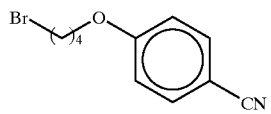

5 g (41.97 mmol) of 4-cyanophenol, 45.3 g (209.87 mmol) of 1,4-dibromobutane, 28.96 g (209.85 mmol) of powdered potassium carbonate and 50 ml of anhydrous DMF are successively introduced into a round-bottomed flask.

The medium is stirred at room temperature for 20 hours.

It is filtered and the filtrate is taken up in 300 ml of ethyl acetate.

The organic phase is washed with a saturated aqueous NaCl solution (3 times 100 ml), dried over MgSO$_4$, filtered and concentrated. 54.4 g of an oil are obtained, which oil is distilled under vacuum produced by a slide vane rotary vacuum pump. The fraction which distils at 100–110° C. under 1 mm of Hg is recovered.

9.6 g (90%) of a colourless oil are obtained.

Examples 33 to 81 are prepared according to one of the methods (a or b) described above.

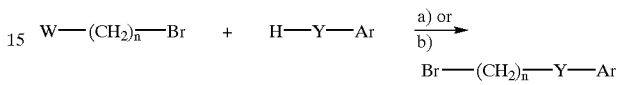

W=Cl, Br; n varies from 3 to 11; Y=O, S; Ar is as defined in formula (I)

| Ex. No. | Starting material | Method | Final product |
|---|---|---|---|
| 33' | Br-(CH$_2$)$_5$-Br | a | Br-(CH$_2$)$_5$-OPh |
| 34 | Br-(CH$_2$)$_5$-Br | a | Br-(CH$_2$)$_5$-O-C$_6$H$_4$-OMe |
| 35 | Br-(CH$_2$)$_4$-Br | a | Br-(CH$_2$)$_4$-O-C$_6$H$_4$-Ph |
| 36 | Br-(CH$_2$)$_4$-Br | a | Br-(CH$_2$)$_4$-O-C$_6$H$_4$-O-CH$_2$Ph |
| 37 | Br-(CH$_2$)$_4$-Br | a | Br-(CH$_2$)$_4$-O-(2-naphthyl) |
| 38 | Br-(CH$_2$)$_4$-Br | a | Br-(CH$_2$)$_4$-O-(1-naphthyl) |
| 39 | Br-(CH$_2$)$_3$-Br | b | Br-(CH$_2$)$_3$-O-C$_6$H$_4$-Et (ortho) |
| 40 | Br-(CH$_2$)$_4$-Br | a | Br-(CH$_2$)$_4$-O-C$_6$H$_4$-OMe |

-continued

| Ex. No. | Starting material | Method | Final product |
|---|---|---|---|
| 41 | Br-(CH₂)₆-Br | a | Br-(CH₂)₆-O-C₆H₅ |
| 42 | Br-(CH₂)₄-Br | a | Br-(CH₂)₄-O-C₆H₄-CH₃ (4-) |
| 43 | Br-(CH₂)₄-Br | a | Br-(CH₂)₄-O-C₆H₄-CH₃ (3-) |
| 44 | Br-(CH₂)₄-Br | a | Br-(CH₂)₄-O-C₆H₄-CH₃ (2-) |
| 45 | Br-(CH₂)₄-Br | a | Br-(CH₂)₄-O-C₆H₄-OMe (3-) |
| 46 | Br-(CH₂)₄-Br | a | Br-(CH₂)₄-O-C₆H₄-Cl (4-) |
| 47 | Br-(CH₂)₄-Br | a | Br-(CH₂)₄-O-C₆H₄-Br (4-) |
| 48 | Br-(CH₂)₄-Br | a | Br-(CH₂)₄-O-C₆H₄-F (4-) |
| 49 | Br-(CH₂)₇-Br | a | Br-(CH₂)₇-O-C₆H₅ |
| 50 | Br-(CH₂)₄-Br | a | Br-(CH₂)₄-O-C₆H₄-OMe (2-) |
| 51 | Br-(CH₂)₄-Br | a | Br-(CH₂)₄-S-C₆H₅ |
| 52 | Br-(CH₂)₄-Br | a | Br-(CH₂)₄-O-C₆H₄-CF₃ (3-) |

-continued

| Ex. No. | Starting material | Method | Final product |
|---|---|---|---|
| 53 | Br-(CH2)4-Br | a | Br-(CH2)4-O-C6H4-F (3-F) |
| 54 | Br-(CH2)4-Br | a | Br-(CH2)4-O-C6H3(F)2 (2,5-difluoro) |
| 55 | Br-(CH2)4-Br | a | Br-(CH2)4-O-benzo[1,3]dioxole |
| 56 | Br-(CH2)4-Br | b | Br-(CH2)4-O-C6H4-F (2-F) |
| 57 | Br-(CH2)4-Br | b | Br-(CH2)4-O-C6H4-OEt (4-OEt) |
| 58 | Br-(CH2)4-Br | b | Br-(CH2)4-O-C6H4-Et (4-Et) |
| 59 | Br-(CH2)4-Br | b | Br-(CH2)4-O-C6F5 (pentafluoro) |
| 60 | Br-(CH2)4-Br | b | Br-(CH2)4-O-C6H4-NO2 (4-NO2) |
| 61 | Br-(CH2)4-Br | b | Br-(CH2)4-O-C6H3(CH3)2 (2,6-dimethyl) |
| 62 | Br-(CH2)4-Br | b | Br-(CH2)4-O-C6H3(OMe)2 (3,5-dimethoxy) |

-continued

| Ex. No. | Starting material | Method | Final product |
|---|---|---|---|
| 63 | Br-(CH₂)₄-Br | b | Br-(CH₂)₄-O-C₆H₃(Cl)(Cl) (3,4-dichloro) |
| 64 | Br-(CH₂)₄-Br | b | Br-(CH₂)₄-O-C₆H₄-On.Bu |
| 65 | Br-(CH₂)₄-Br | b | Br-(CH₂)₄-O-(2-pyridyl) |
| 66 | Br-(CH₂)₄-Br | b | Br-(CH₂)₄-O-C₆H₄-CN (3-CN) |
| 67 | Br-(CH₂)₃-Cl | b | Cl-(CH₂)₃-O-C₆H₄-CH₂-Ph |
| 68 | Br-(CH₂)₄-Br | b | Br-(CH₂)₄-O-C₆H₄-Cl (3-Cl) |
| 69 | Br-(CH₂)₅-Br | b | Br-(CH₂)₅-O-C₆H₄-CN |
| 70 | Br-(CH₂)₃-Br | b | Br-(CH₂)₃-O-C₆H₄-CN |
| 71 | Br-(CH₂)₄-Br | b | Br-(CH₂)₄-O-C₆H₄-Et |
| 72 | Br-(CH₂)₄-Br | b | Br-(CH₂)₄-O-C₆H₄-CF₃ |
| 73 | Br-(CH₂)₅-Br | b | Br-(CH₂)₅-O-C₆H₄-CH₂-Ph |
| 74 | Br-(CH₂)₄-Br | b | Br-(CH₂)₄-O-C₆H₄-CH₂-Ph |

-continued

| Ex. No. | Starting material | Method | Final product |
|---|---|---|---|
| 75 | Cl~(CH2)3~Br | b | Cl~(CH2)3~O-C6H4-CH3 |
| 76 | Br~(CH2)4~Br | b | Br~(CH2)4~O-C6H4-NH-C(=O)-CH3 |
| 77 | Br~(CH2)4~Br | b | Br~(CH2)4~O-C6H4-I |
| 78 | Br~(CH2)4~Br | b | Br~(CH2)4~O-C6H4-On.Pr |
| 79 | Cl~(CH2)3~Br | b | Cl~(CH2)3~O-C6H4-C(=O)-C6H5 |
| 80 | Cl~(CH2)3~Br | b | Cl~(CH2)3~O-C6H4-OEt |
| 81 | Br~(CH2)5~Br | b | Br~(CH2)5~O-C6H4-OEt |
| 82 | Br~(CH2)4~Br | a | Br~(CH2)4~O-C6H4-OPh |

Example 83

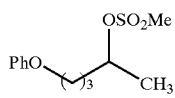

3.07 g (30.29 mmol) of triethylamine are added at 0° C. to a solution of 4.57 g (25.35 mmol) of 4-phenoxy-2-butanol in 30 ml of $CH_2Cl_2$. 3.47 g (30.29 mmol) of methyl chloride are added dropwise and the medium is stirred for 4 hours at room temperature.

The organic phase is washed with 10 ml of 1.2 N HCl, dried over $MgSO_4$, filtered and then concentrated under vacuum. 6.5 g (yield 99%) of an oily residue are obtained.

Example 84

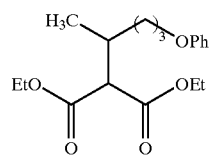

12.1 g (75.48 mmol) of diethyl malonate, 11.46 g (75.48 mmol) of cesium fluoride and 100 ml of anhydrous DMF are successively added to a round-bottomed flask under an inert atmosphere. The medium is stirred for 1 hour at room temperature. A solution of 6.5 g (25.16 mmol) of the mesylate prepared in Example 83 in 25 ml of anhydrous DMF is added. The medium is heated at 60° C. for 24 hours.

The medium is diluted with 100 ml of ethyl acetate. It is washed with water (3 times with 30 ml), with a saturated aqueous $NaHCO_3$ solution. The organic phase is dried over $MgSO_4$, filtered and concentrated. 21.4 g of residue are obtained, which residue is distilled using a slide vane rotary vacuum pump so as to remove the excess of DMF and diethyl malonate. The residue (6.4 g) is chromatographed on silica (eluent:

ether-petroleum ether 10/90). 2.82 g (yield 35%) of the expected malonate are obtained.

Example 85

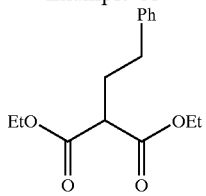

The product of Example 85 is prepared from 2-bromoethylphenyl diethyl malonate according to the same method as that described in Example 7.

Yield=85%, yellow oil.

Example 86

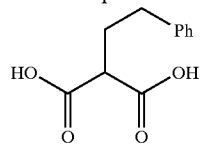

6.02 g (22.78 mmol) of the malonic diester of Example 84 are diluted with 26 ml of water. 2.25 g (56.2 mmol) of sodium hydroxide pellets are added.

The medium is stirred and heated under reflux for 1 hour 30 min.

The medium is diluted with water and washed with $Et_2O$ (once 15 ml).

The aqueous phase is cooled and acidified with concentrated aqueous hydrochloric acid solution to pH=1.

The medium is -extracted with $Et_2O$ (twice 25 ml). The ethereal phases are combined, dried over $MgSO_4$, filtered and concentrated.

4.1 g (86%) of a white solid are obtained.

Example 87

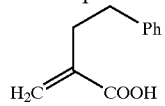

1.44 g (19.7 mmol) of diethylamine and then 0.99 g (33 mmol) of paraformaldehyde are added to a solution of 4.1 g (19.7 mmol) of the malonic diacid of Example 86 in 20 ml of AcOEt.

The medium is heated under reflux for 30 minutes.

The solution is then cooled using a bath of ice and water, diluted with 10 ml of water and then acidified with a 3 N HCl solution to pH=1. The aqueous phase is removed. The organic phase is washed with water (once 10 ml), dried over $MgSO_4$, filtered and concentrated.

3.23 g (93%) of a white solid are obtained.

Example 88

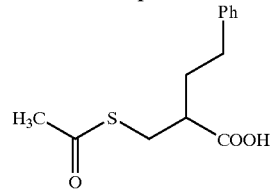

The acrylic acid of Example 87 is heated at 70° C. and then overnight with 2.23 g (29.34 mmol) of thioacetic acid.

The solution is diluted with 10 ml of $Et_2O$ and then concentrated under vacuum.

4.6 g (99%) of the desired acid are thus obtained.

Examples 89 to 145 are prepared according to the same reaction sequence as that described in Example 88:

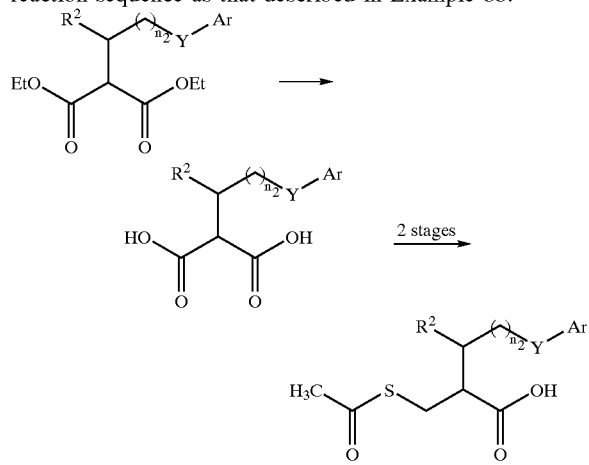

| Ex. No. | Starting material | Acid prepared |
|---|---|---|
| 89 | ex. 31 | 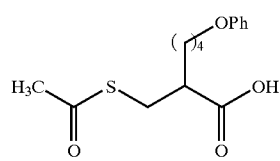 |

-continued
| Ex. No. | Starting material | Acid prepared |
|---|---|---|
| 90 | ex. 84 | 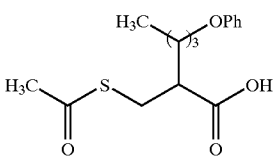 |
| 91 | ex. 33 | 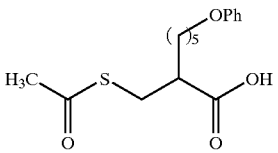 |
| 92 | ex. 34 | 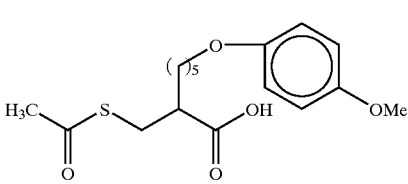 |
| 93 | ex. 35 | 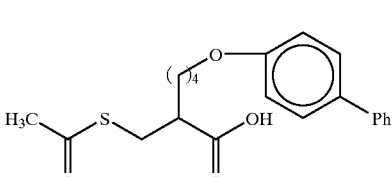 |
| 94 | ex. 36 | 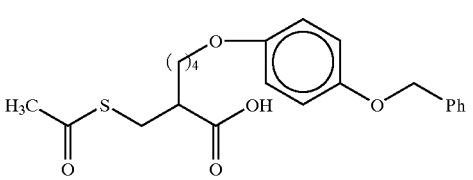 |
| 95 | ex. 37 | 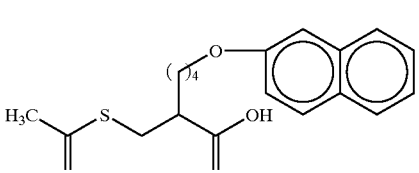 |
| 96 | ex. 38 | 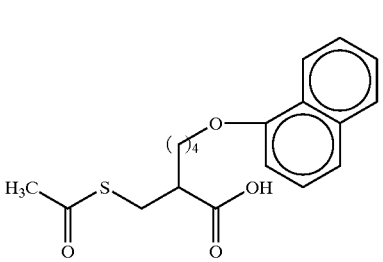 |
| 97 | ex. 39 | 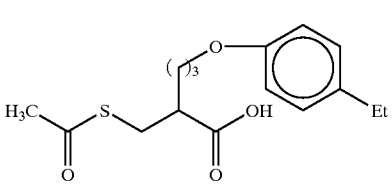 |

-continued

| Ex. No. | Starting material | Acid prepared |
|---|---|---|
| 98 | ex. 40 | $CH_3C(O)S-CH_2-CH(COOH)-(CH_2)_4-O-C_6H_4-OMe$ (4-OMe) |
| 99 | ex. 41 | $CH_3C(O)S-CH_2-CH(COOH)-(CH_2)_6-O-C_6H_5$ |
| 100 | ex. 42 | $CH_3C(O)S-CH_2-CH(COOH)-(CH_2)_4-O-C_6H_4-CH_3$ (4-CH₃) |
| 101 | ex. 43 | $CH_3C(O)S-CH_2-CH(COOH)-(CH_2)_4-O-C_6H_4-CH_3$ (3-CH₃) |
| 102 | ex. 44 | $CH_3C(O)S-CH_2-CH(COOH)-(CH_2)_4-O-C_6H_4-CH_3$ (2-CH₃) |
| 103 | ex. 45 | $CH_3C(O)S-CH_2-CH(COOH)-(CH_2)_4-O-C_6H_4-OMe$ (3-OMe) |
| 104 | ex. 46 | $CH_3C(O)S-CH_2-CH(COOH)-(CH_2)_4-O-C_6H_4-Cl$ (3-Cl) |
| 105 | ex. 47 | $CH_3C(O)S-CH_2-CH(COOH)-(CH_2)_4-O-C_6H_4-Br$ (3-Br) |

-continued

| Ex. No. | Starting material | Acid prepared |
|---|---|---|
| 106 | ex. 48 | CH₃C(=O)S-CH₂-CH(COOH)-(CH₂)₄-O-C₆H₄-F |
| 107 | ex. 49 | CH₃C(=O)S-CH₂-CH(COOH)-(CH₂)₇-O-C₆H₅ |
| 108 | ex. 50 | CH₃C(=O)S-CH₂-CH(COOH)-(CH₂)₄-O-C₆H₄(OMe) |
| 109 | ex. 51 | CH₃C(=O)S-CH₂-CH(COOH)-(CH₂)₄-S-C₆H₅ |
| 110 | ex. 52 | CH₃C(=O)S-CH₂-CH(COOH)-(CH₂)₄-O-C₆H₄-CF₃ |
| 111 | ex. 53 | CH₃C(=O)S-CH₂-CH(COOH)-(CH₂)₄-O-C₆H₄-F |
| 112 | ex. 54 | CH₃C(=O)S-CH₂-CH(COOH)-(CH₂)₄-O-C₆H₃(F)₂ |
| 113 | ex. 55 | CH₃C(=O)S-CH₂-CH(COOH)-(CH₂)₄-O-C₆H₃(OCH₂O) |

-continued
| Ex. No. | Starting material | Acid prepared |
|---|---|---|
| 114 | ex. 56 | 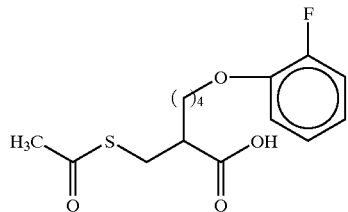 |
| 115 | ex. 57 | 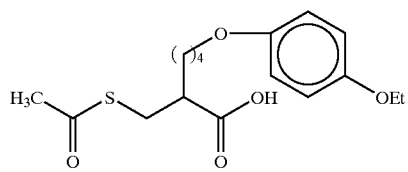 |
| 116 | ex. 58 | 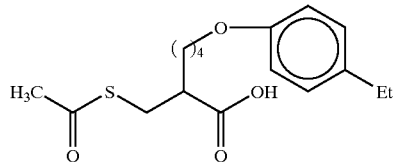 |
| 117 | ex. 59 | 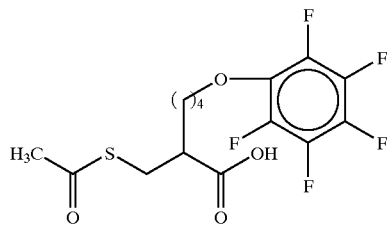 |
| 118 | ex. 60 | 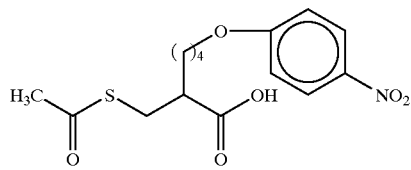 |
| 119 | Br(CH₂)₂S-CH₂-Ph | 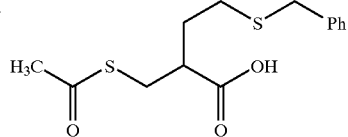 |
| 120 | Br(CH₂)₂SPh | 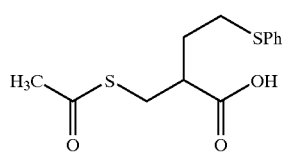 |
| 121 | PhO(CH₂)₃Br | 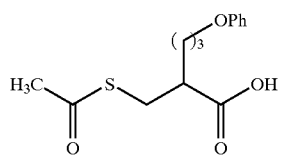 |

-continued

| Ex. No. | Starting material | Acid prepared |
|---|---|---|
| 122 | ex. 62 | AcS-CH2-CH(COOH)-(CH2)4-O-C6H3(OMe)2 (2,5-dimethoxyphenyl) |
| 123 | ex. 63 | AcS-CH2-CH(COOH)-(CH2)4-O-C6H3Cl2 (3,4-dichlorophenyl) |
| 124 | ex. 64 | AcS-CH2-CH(COOH)-(CH2)4-O-C6H4-On.Bu |
| 125 | ex. 65 | AcS-CH2-CH(COOH)-(CH2)4-O-(pyridyl) |
| 126 | ex. 67 | AcS-CH2-CH(COOH)-(CH2)3-O-C6H4-Ph |
| 127 | ex. 68 | AcS-CH2-CH(COOH)-(CH2)4-O-C6H4-Cl |
| 128 | ex. 71 | AcS-CH2-CH(COOH)-(CH2)4-O-C6H4-Et |
| 129 | ex. 72 | AcS-CH2-CH(COOH)-(CH2)4-O-C6H4-CF3 |

-continued

| Ex. No. | Starting material | Acid prepared |
|---|---|---|
| 130 | ex. 73 | H₃C-C(=O)-S-CH₂-CH(COOH)-(CH₂)₅-O-C₆H₄-CH₂-Ph |
| 131 | ex. 74 | H₃C-C(=O)-S-CH₂-CH(COOH)-(CH₂)₄-O-C₆H₄-CH₂-Ph |
| 132 | ex. 39 | H₃C-C(=O)-S-CH₂-CH(COOH)-(CH₂)₃-O-C₆H₄-Et |
| 133 | ex. 75 | H₃C-C(=O)-S-CH₂-CH(COOH)-(CH₂)₃-O-C₆H₄-CH₃ |
| 134 | ex. 76 | H₃C-C(=O)-S-CH₂-CH(COOH)-(CH₂)₄-O-C₆H₄-NH-C(=O)-CH₃ |
| 135 | ex. 77 | H₃C-C(=O)-S-CH₂-CH(COOH)-(CH₂)₄-O-C₆H₄-I |
| 136 | ex. 78 | H₃C-C(=O)-S-CH₂-CH(COOH)-(CH₂)₄-O-C₆H₄-On.Pr |
| 137 | ex. 79 | H₃C-C(=O)-S-CH₂-CH(COOH)-(CH₂)₃-O-C₆H₄-C(=O)-Ph |

-continued

| Ex. No. | Starting material | Acid prepared |
|---|---|---|
| 138 | ex. 80 | CH₃C(=O)S-CH₂-CH(COOH)-(CH₂)₃-O-C₆H₄-OEt |
| 139 | ex. 81 | CH₃C(=O)S-CH₂-CH(COOH)-(CH₂)₅-O-C₆H₄-OEt |
| 140 | ex. 61 | CH₃C(=O)S-CH₂-CH(COOH)-(CH₂)₄-O-(2,6-dimethylphenyl) |
| 141 | Br-(CH₂)₃-Ph | CH₃C(=O)S-CH₂-CH(COOH)-(CH₂)₃-Ph |
| 142 | Cl-(CH₂)₂-OPh | CH₃C(=O)S-CH₂-CH(COOH)-(CH₂)₂-OPh |
| 143 | Cl-(CH₂)₆-Ph | CH₃C(=O)S-CH₂-CH(COOH)-(CH₂)₆-Ph |
| 144 | Cl-(CH₂)₄-Ph | CH₃C(=O)S-CH₂-CH(COOH)-(CH₂)₄-Ph |
| 145 | ex. 82 | CH₃C(=O)S-CH₂-CH(COOH)-(CH₂)₄-O-C₆H₄-OPh |

Example 146

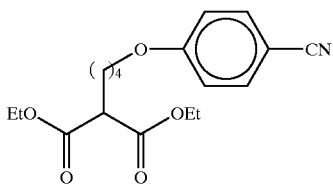

The malonic diester of Example 146 is prepared from diethyl malonate and the brominated derivative of Example 32 according to the same method as that described in Example 7.

Yield: 81%, yellow solid.

Example 147

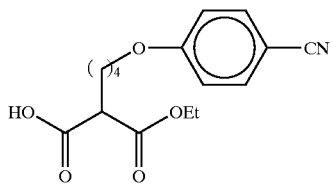

The diester of Example 146 is monosaponified using the same method as that described for Example 8.

Yield: 90%, yellow viscous oil.

Example 148

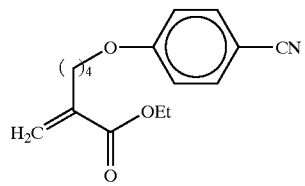

There are introduced into a round-bottomed flask 8.45 g (27.70 mmol) of the acid of Example 147 in solution in 50 ml of $CH_2Cl_2$ which is cooled using an ice-water bath.

2.02 g (27.67 mmol) of diethylamine and 2.8 ml of a 37% aqueous solution of formaldehyde are added.

The temperature is allowed to rise to room temperature and then the medium is stirred overnight.

The organic phase is washed with a 1N HCl solution (twice 20 ml), dried over $MgSO_4$, filtered and concentrated.

7.26 (76%) of a yellow solid are obtained.

Example 149

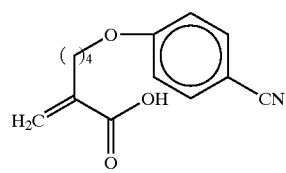

7.2 g (26.37 mmol) of the ester of Example 148 are dissolved with 29 ml of acetone and 9 ml of water. The medium is cooled to about 5° C. and 32 ml of N NaOH are added. The temperature is allowed to return to room temperature and then the medium is heated under reflux for 6 hours.

The medium is concentrated under vacuum and the residual aqueous phase is washed with ethyl ether (twice 20 ml).

The aqueous phase is cooled and then acidified to pH=1 with a 3 N HCl solution. The precipitate obtained is filtered, washed with water (once 20 ml) and dried under vacuum over $P_2O_5$ to a constant mass.

4.05 g (63%) of a white solid are obtained. Example 150

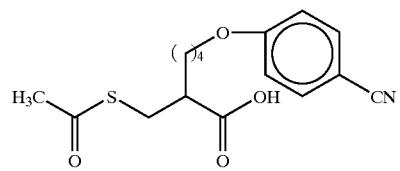

4.05 g (16.59 mmol) of the acid of Example 149 and 2.02 g (26.55 mmol) of thioacetic acid are heated at 70° C. overnight.

The medium is diluted with 20 ml of ethyl ether and then concentrated under vacuum. The residue is chromatographed on silica (eluent 60/40 ethyl ether/petroleum ether).

2.04 g (38%) of the desired product are obtained.

Examples 151 to 153 are prepared according to the same reaction sequence as that described for Example 150.

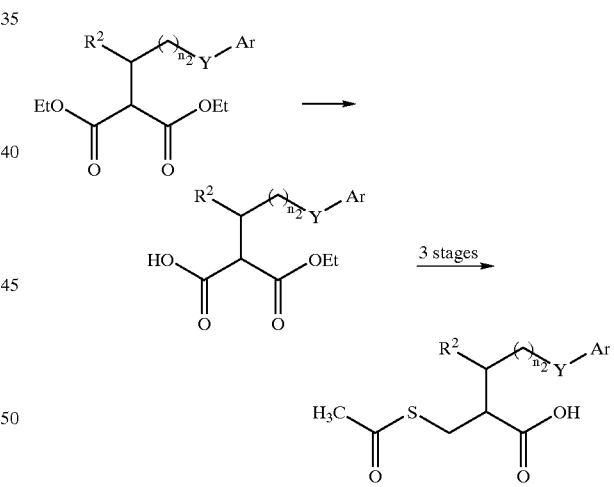

| Ex. No. | Starting material | Acid prepared |
|---|---|---|
| 151 | ex. 66 | 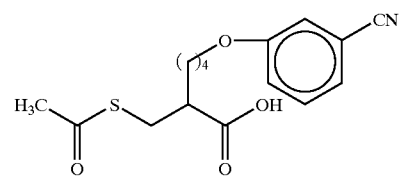 |

-continued

| Ex. No. | Starting material | Acid prepared |
|---|---|---|
| 152 | ex. 69 | 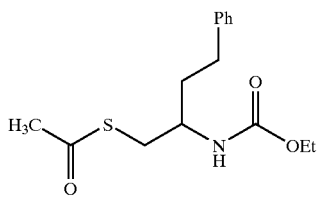 |
| 153 | ex. 70 | |

Example 154

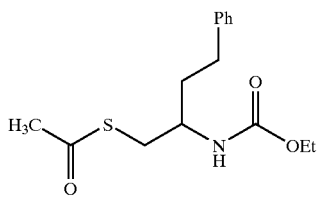

2.9 g (10.53 mmol) of DPPA and 1.06 g (10.47 mmol) of triethylamine are added dropwise to 2.5 g (10 mmol) of the acid of Example 88 in solution in 10 ml of toluene. The mixture is heated at 80° C. for 1 hour. After returning to room temperature, 0.73 ml (12.5 mmol) of ethanol is added and the medium is heated at 80° C. overnight.

The medium is diluted with 20 ml of toluene and successively washed with water (once 10 ml), a saturated aqueous $NaHCO_3$ solution (once 10 ml) and water (once 10 ml).

The organic phase is dried over $MgSO_4$, filtered and concentrated. 3.1 g of an oily residue are obtained, which residue is chromatographed on silica (eluent: ether-petroleum ether 3/7). 1.5 g (yield 50%) of a white solid are obtained.

Example 155

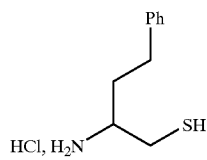

3 ml of a 10 N aqueous sodium hydroxide solution and 0.3 ml of EtOH are added to 0.92 g (3.1 mmol) of the product of Example 154 under an inert atmosphere.

The medium is heated under reflux for 1 hour 30 minutes.

The medium is cooled to 0° C. and acidified dropwise to pH=1 with a 1 N HCl solution. The medium is washed with ether (twice 10 ml) and the aqueous phase is evaporated to dryness. The solid residue is dried under vacuum over $P_2O_5$ and then extracted with $CHCl_3$ under reflux (twice 20 ml).

The organic phases are combined and then concentrated under vacuum. The residue is then triturated with 10 ml of anhydrous ether. The medium is filtered and the precipitate washed with ether (10 ml). After drying under vacuum, 0.37 g (yield: 50%) of the desired product is obtained.

$^1$H NMR (200 MHz, $D_2O$): 7.4 to 7.0 (m, 5H); 4.65 (s, 4H); 3.4 to 3.15 (m, 1H); 3.0 to 2.5 (m, 4H); 2.05 to 1.7 (m, 2H).

Examples 156 to 180 are prepared according to the same method as that described in Example 155.

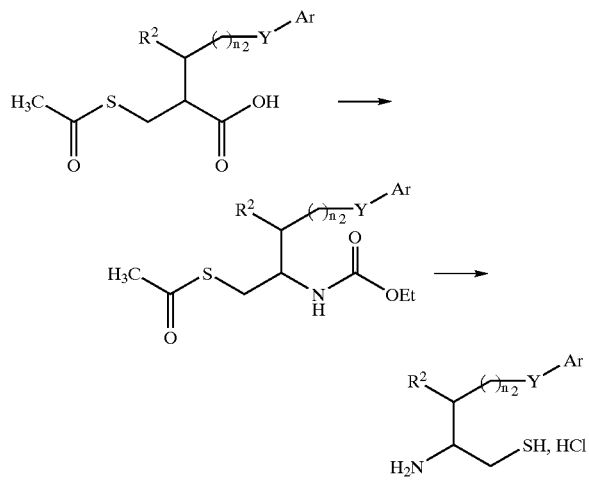

| Ex. No. (conf.) | Compound | Starting material | Analyses |
|---|---|---|---|
| 156 (RS) | (structure with OPh, n=4, HCl·H₂N, SH) | 89 | $^1$H NMR (200MHz, $CDCl_3$): 8.5(s, 3H); 7.4 to 7.15(m, 2H); 7.0 to 6.75(m, 3H); 3.95(t, 2H, J=6Hz); 3.5 to 3.25(m, 1H); 3.05 to 2.7(m, 2H); 2.0(t, 1H, J=9Hz; 2.05 to 1.4(m, 6H). |
| 157 (RS) | (structure with OPh, n=5, HCl·H₂N, SH) | 91 | $^1$H NMR (200MHz, $CDCl_3$): 8.5(s, 3H); 7.35 to 7.15(m, 2H); 7.0 to 6.75(m, 3H); 3.9(t, 2H, J=6Hz); 3.5 to 3.25(m, 1H); 3.05 to 2.7(m, 2H); 2.0(t, 1H, J=9Hz); 2.1 to 1.3(m, 8H) |

-continued

| Ex. No. (conf.) | Compound | Starting material | Analyses |
|---|---|---|---|
| 158 (RS) | (structure: HCl, H₂N–CH(CH₂SH)–(CH₂)₅–O–C₆H₄–OMe) | 92 | ¹H NMR (200MHz, CDCl₃): 8.5(s, 3H); 6.95 to 6.75(m, 4H); 3.9(t, 2H, J=6Hz); 3.75(s, 3H); 3.5 to 3.2(m, 1H); 3.05 to 2.75(m, 2H); 2.0(t, 1H, J=8.8Hz); 2 to 1.3(m, 8H) |
| 159 (RS) | (structure: HCl, H₂N–CH(CH₂SH)–(CH₂)₄–O–C₆H₄–OMe) | 98 | ¹H NMR (200MHz, CDCl₃): 8.5(s, 3H); 6.9 to 6.7(m, 4H); 3.9(t, 2H, J=6Hz); 3.75(s, 3H); 3.5 to 3.25(m, 1H); 3.05 to 2.75(m, 2H); 2.0(t, 1H, J=8Hz); 2.0 to 1.4(m, 6H) |
| 160 (RS) | (structure: HCl, H₂N–CH(CH₂SH)–(CH₂)₄–O–C₆H₄–CH₃) | 100 | ¹H NMR (200MHz, CDCl₃): 8.5(s, 3H); 7.05 and 6.75(AB, 4H, J=8Hz); 3.9(t, 2H, J=6 Hz); 3.5 to 3.25(m, 1H); 3.05 to 2.75(m, 2H); 2.2(s, 3H); 2.0(t, 1H, J=8Hz); 2.0 to 1.4(m, 6H) |
| 161 (RS) | (structure: HCl, H₂N–CH(CH₂SH)–(CH₂)₄–O–C₆H₄–CH₃) | 101 | ¹H NMR (200MHz, CDCl₃): 8.5(s, 3H); 7.25 to 7.05(m, 1H); 6.85 to 6.55(m, 3H); 3.9(t, 2H, J=6Hz); 3.55 to 3.25(m, 1H); 3.1 to 2.65(m, 2H); 2.25(s, 3H); 2(t, 1H, J=8Hz); 2.0 to 1.4 (m, 6H) |
| 162 (RS) | (structure: HCl, H₂N–CH(CH₂SH)–(CH₂)₄–O–C₆H₄–OMe) | 103 | ¹H NMR (200MHz, CDCl₃): 8.5(s, 3H); 7.3 to 7.0(m, 1H); 6.65 to 6.25(m, 3H); 3.9(t, 2H, J=6Hz); 3.75(s, 3H); 3.55 to 3.25(m, 1H); 3.1 to 2.65(m, 2H); 2.0(t, 1H, J=8Hz); 2.05 to 1.35 (m, 6H) |
| 163 (RS) | (structure: HCl, H₂N–CH(CH₂SH)–(CH₂)₄–O–C₆H₄–Cl) | 104 | ¹H NMR (200MHz, CDCl₃): 8.5(m, 3H); 7.15 and 6.65(AB, 4H, J=7.2Hz); 3.8(m, 2H); 3.5 to 3.2(m, 1H); 3.1 to 2.6(m, 2H); 2.1 to 1.15(m, 7H) |
| 164 (RS) | (structure: HCl, H₂N–CH(CH₂SH)–(CH₂)₄–O–C₆H₄–Br) | 105 | ¹H NMR (200MHz, DMSO-d6): 8.25(m, 3H); 7, 4 and 6.85(AB, 4H, J=8Hz); 3.85(t, 2H, J=6, 4Hz); 3.3 to 3.05(m, 1H); 3.0 to 2.85(m, 1H); 2.85 to 2.65(m, 2H); 1.85 to 1.3(m, 6H) |
| 165 (RS) | (structure: HCl, H₂N–CH(CH₂SH)–(CH₂)₄–O–C₆H₄–F) | 106 | ¹H NMR (200MHz, CDCl₃): 8.4(m, 3H); 7.1 to 6.65(m, 4H); 3.75(t, 2H, J=4Hz); 3.5 to 3.25 (m, 1H); 3.1 to 2.65(m, 2H); 1.9(t, 1H, J=8 Hz); 2.10 to 1.35(m, 7H) |
| 166 (RS) | (structure: HCl, H₂N–CH(CH₂SH)–(CH₂)₄–O–C₆H₄–OMe, ortho) | 108 | ¹H NMR (200MHz, CDCl₃): 8.45(s, 3H); 7.1 to 6.6(m, 4H); 3.95(t, 2H, J=6Hz); 3.8(s, 3H); 3.55 to 3.25(m, 1H); 3.15 to 2.7(m, 2H); 2.25 to 1.4(m, 7H) |
| 167 (RS) | (structure: HCl, H₂N–CH(CH₂SH)–(CH₂)₄–S–Ph) | 109 | ¹H NMR (200MHz, CDCl₃): 8.5(s, 3H); 7.4 to 7.05(m, 5H); 3.45 to 3.2(m, 1H); 3.05 to 2.65 (m, 4H); 1.95(t, 1H, J=8.8Hz); 1.9 to 1.35(m, 6H) |
| 168 (RS) | (structure: HCl, H₂N–CH(CH₂SH)–(CH₂)₄–O–benzodioxole) | 113 | ¹H NMR (200MHz, CDCl₃) 8.4(m, 3H); 6.65 (d, 1H, J=8Hz); 6.45(s, 1H); 6.25(d, 1H, J= 8Hz); 5.8(s, 2H); 3.9 to 3.75(m, 2H); 3.5 to 3.3 (m, 1H); 3.05 to 2.7(m, 2H); 2.05 to 1.35(m, 7H) |

-continued

| Ex. No. (conf.) | Compound | Starting material | Analyses |
|---|---|---|---|
| 169 (RS) | HCl, H₂N–CH(CH₂SH)–(CH₂)₄–O–C₆H₄–OEt | 115 | ¹H NMR (200MHz, CDCl₃): 8.45(s, 3H); 6.9 to 6.65(m, 4H); 3.95(q, 2H, J=7Hz); 3.85(t, 2H, J=6Hz); 3.5 to 3.3(m, 1H); 3.05 to 2.7(m, 2H); 2.0(t, 1H, J=8Hz); 2.0 to 1.45(m, 6H); 1.35(t, 2H, J=7Hz) |
| 170 (RS) | HCl, H₂N–CH(CH₂SH)–(CH₂)₄–O–C₆H₄–Et | 116 | ¹H NMR (200MHz, CDCl₃): 8.5(s, 3H); 7.1 and 6.8(AB, 4H, J=8Hz); 3.9(t, 2H, J=7Hz); 3.55 to 3.25(m, 1H); 3.05 to 2.7(m, 2H); 2.6(q, 2H, J=7Hz); 2.0(t, 1H, J=8Hz); 2.0 to 1.4 (m, 6H); 1.2(t, 3H, J=7Hz) |
| 171 (RS) | HCl, H₂N–CH(CH₂SH)–(CH₂)₃–Ph | 141 | ¹H NMR (200MHz, CDCl₃): 8.45(m, 3H); 7.35 to 7.05(m, 5H); 3.45 to 3.25(m, 1H); 3.0 to 2.5(m, 4H); 1.9(t, 1H, J=8Hz); 2.0 to 1.55(m, 4H). |
| 172 (RS) | HCl, H₂N–CH(CH₂SH)–(CH₂)₂–OPh | 142 | ¹H NMR (200MHz, D₂O), 7.45 to 7.2(m, 2H); 7.0 to 6.85(m, 3H); 4.6(s, 4H); 4.05(t, 2H, J=6Hz); 3.65 to 3.5(m, 1H); 3.0 to 2.65(m, 2H); 2.2 to 2.0(m, 2H) |
| 173 (RS) | HCl, H₂N–CH(CH₂SH)–(CH₂)₄–Ph | 144 | ¹H NMR (D₂O, 200MHz): 7.2 to 7.0(m, 5H); 4.6(s, 2H); 3.2(q, 2H, J=4.6Hz); 2.75 to 2.65 (m, 1H); 2.6 to 2.5(m, 1H); 2.5(t, 2H, J=7.5 Hz); 1.6 to 1.4(m, 4H); 1.25 to 1.2(m, 2H) |
| 174 (RS) | HCl, H₂N–CH(CH₂SH)–(CH₂)₂–SPh | 120 | ¹H NMR (200MHz, D₂O): 7.35 to 7.0(m, 5H); 4.6(s, 4H); 3.45 to 3.3(m, 1H); 2.8(t, 2H, J=6.5Hz); 2.75 to 2.45(m, 2H); 1.9 to 1.7(m, 2H) |
| 175 (RS) | HCl, H₂N–CH(CH₂SH)–(CH₂)₄–O–C₆H₃(CH₃)₂ | 140 | ¹H NMR (200MHz, CDCl₃): 8.55(s, 3H); 7 to 6.8(m, 3H); 3.8 to 2.65(m, 2H); 3.45 to 3.25(m, 1H); 3.0 to 2.75(m, 2H); 2.2(s, 6H); 1.95(t, 1H, J=8.0Hz); 2.0 to 1.5(m, 6H) |
| 176 (RS) | HCl, H₂N–CH(CH₂SH)–(CH₂)₂–S–CH₂–Ph | 119 | ¹H NMR (200MHz, CDCl₃): 8.4(s, 3H); 7.35 to 7.1(m, 5H); 3.65(s, 2H); 3;65 to 3.55(m, 1H); 2.95 to 2.4(m, 4H); 2.25 to 2(m, 2H); 1.95(t, 1H, J=7.5Hz) |
| 177 (RS) | HCl, H₂N–CH(CH₂SH)–(CH₂)₃–OPh | 121 | ¹H NMR (200MHz, D₂O): 7.3 to 7.1(m, 2H); 7.0 to 6.75(m, 3H); 4.65(s, 4H); 3.8(t, 2H, J= 4 Hz); 3.4 to 3.2(m, 1H); 2.9 to 2.5(m, 2H); 1.85 to 1.6(m, 4H) |
| 178 (RS) | HCl, H₂N–CH(CH₂SH)–(CH₂)₄–O–C₆H₄–CH₃ | 102 | ¹H NMR (200MHz, CDCl₃): 8.5(s, 3H); 7.2 to 7.0(m, 2H); 6.9 to 6.7(m, 2H); 3.95(t, 2H, J= 6Hz); 2.5 to 3.25(m, 1H); 3.1 to 2.7(m, 2H); 2.2(s, 3H); 2.0(t, 1H, J=8Hz); 2.0 to 1.4 (m, 6H) |

| Ex. No. (conf.) | Compound | Starting material | Analyses |
|---|---|---|---|
| 179 (RS) | 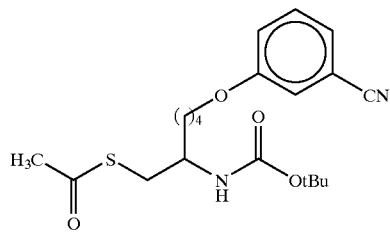 | 145 | $^1$H NMR (200MHz, CDCl$_3$): 8.5(s, 3H); 7.5 to 6.5(m, 9H); 3.9(t, 2H, J=6Hz); 3.55 to 3.25 (m, 1H); 3.15 to 2.65(m, 2H); 2.0(t, 1H, J=8 Hz); 2.05 to 1.3(m, 6H) |
| 180 (RS) | 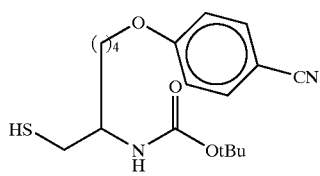 | 150 | $^1$H NMR (200MHz, DMSO-d6): 12.6(broad s, 1H); 8.4(broad s, 3H); 7.9 and 7.0(AB, 4H, X=9Hz); 4.0(t, 2H, J=6.7Hz); 3.55 to 2.5(m, 4H); 2.0 to 1.2(m, 6H) |

Example 181

1.74 g (6.35 mmol) of DPPA and then 0.64 g (6.35 mmol) of triethylamine are successively added to 2.04 g (6.35 mmol) of the acid of Example 150 in solution in 16 ml of tBuOH. The reaction medium is heated under reflux overnight and then concentrated under vacuum. The residue is taken up in 40 ml of ethyl acetate and is then successively washed with water (once 10 ml), a saturated aqueous NaHCO$_3$ solution (twice 10 ml) and then water (once 10 ml).

The organic phase is dried over MgSO$_4$, filtered and then concentrated under vacuum. An oily residue is obtained which is purified by flash chromatography on silica using the ether-petroleum ether (4/7) mixture and then ether as eluents. 1.6 g (yield 64%) of an oily residue are obtained.

Example 182

4.9 ml of a 1 N aqueous sodium hydroxide solution are added to 1.6 g (4.08 mmol) of the thioester of Example 181 under an inert atmosphere in solution in 10 ml of MeOH. The reaction medium is stirred for 45 minutes at room temperature and then concentrated under vacuum.

The residue is taken up in ether (30 ml) and the medium is successively washed with water (once 8 ml) and then with a 1 N aqueous hydrochloric acid solution (once 8 ml). The ethereal phase is dried over MgSO$_4$, filtered and then evaporated to dryness. The oily residue is purified by flash chromatography on silica using the ether-petroleum ether (1/1) mixture as eluent. 0.87 g (yield 60.8%) of the desired compound is obtained in the form of a yellow oil.

Example 183

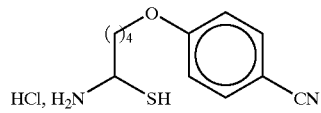

A solution of 0.87 g (2.48 mmol) of the compound of Example 182 in 9 ml of MeOH is cooled to −50° C. using an acetone/dry ice bath. Gaseous HCl is then added to the surface of the reaction medium so that the temperature does not exceed −10° C. Once this addition is no longer exothermic, the reaction medium is allowed to return to room temperature and concentrated under vacuum. 0.66 g of a white solid is obtained which is dried under vacuum over P$_2$O$_5$.

The solid is then triturated in 10 ml of anhydrous Et$_2$O. The medium is filtered, the solid washed with 10 ml of Et$_2$O and dried in a desiccator. 0.58 g (yield 81.5%) of the expected product is obtained.

$^1$H NMR (200 MHz, CDCl$_3$): 8.5 (s, 3H); 7.5 and 6.85 (AB, 4H, Japp.=8 Hz); 3.95 (t, 2H, J=6.5 Hz); 3.5 to 3.35 (m, 1H); 3.05 to 2.7 (m, 2H); 2.1 to 1.4 (m, 6H); 1.9 (t, 1H, J=8 Hz).

Examples 184 to 218 are prepared according to the same method as that described for Example 183.

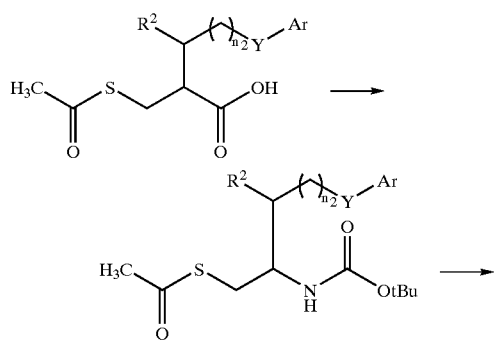

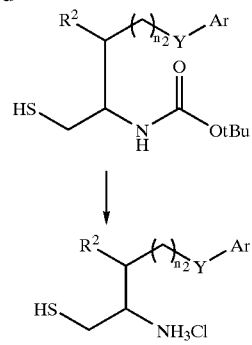

| Ex. No. (conf.) | Compound | Starting material | Analyses |
|---|---|---|---|
| 184 (RS) | H₃C-(　)₃-OPh, SH, HCl, H₂N | ex. 90 | $^1$H NMR (200 MHz, CDCl$_3$): 8.5(m, 3H); 7.4 to 7.15(m, 2H), 7.0 to 6.75(m, 3H); 4.05 to 3.8(m, 2H); 3.35 to 3.10(m, 1H); 3.0 to 2.7(m, 2H); 2.25 to 1.3(m, 7H); 1.2 to 0.9(m, 3H) |
| 185 (RS) | (　)₄-O-C₆H₄-Ph, SH, HCl, H₂N | ex. 93 | $^1$H NMR (200 MHz, CDCl$_3$): 8.5(s, 3H); 7.55 to 7.2(m, 7H); 7.0 to 6.85(m, 2H); 4.05 to 3.9(m, 2H); 3.5 to 3.3(m, 1H); 3.05 to 2.75(m, 2H); 2.05 to 1.5(m, 7H) |
| 186 (RS) | (　)₄-O-C₆H₄-OCH₂Ph, SH, HCl, H₂N | ex. 94 | $^1$H NMR (200 MHz, CDCl$_3$): 8.5(s, 3H); 7.45 to 7.2(m, 5H); 6.95 to 6.7(m, 4H); 4.95(s, 2H); 3.85(t, 2H, J = 4 Hz); 3.5 to 3.25(m, 1H); 3.0 to 2.7(m, 2H); 2.05 to 1.4(m, 7H) |
| 187 (RS) | (　)₄-O-naphthyl, SH, HCl, H₂N | ex. 95 | $^1$H NMR (200 MHz, CDCl$_3$): 8.5(s, 3H); 7.8 to 7.55(m, 3H); 7.5 to 7.0 (m, 4H); 3.9(t, 2H, J=4 Hz); 3.5 to 3.25(m, 1H); 3.0 to 2.7(m, 2H); 2.1 to 1.4(m, 7H) |
| 188 (RS) | (　)₄-O-naphthyl, SH, HCl, H₂N | ex. 96 | $^1$H NMR (200 MHz, CDCl$_3$): 8.5(s, 3H); 8.3 to 8.15(m, 1H); 7.8 to 7.65 (m, 1H); 7.6 to 7.2(m, 4H); 6.7(d, 1H, J=6.6 Hz); 4 (t, 2H, J=4 Hz); 3.45 to 3.2(m, 1H); 3.0 to 2.65(m, 2H); 2.1 to 1.5(m, 7H) |
| 189 (RS) | (　)₆-OPh, SH, HCl, H₂N | ex. 99 | $^1$H NMR (200 MHz, CDCl$_3$): 8.5(s, 3H); 7.4 to 7.1(m, 2H); 7.05 to 6.7 (m, 3H); 3.9(t, 2H, J=6 Hz); 3.5 to 3.2(m, 1H); 3.05 to 2.5(m, 2H); 2.0(t, 1H, J=8 Hz); 2.0 to 1.1(m, 10H) |
| 190 (RS) | (　)₇-OPh, SH, HCl, H₂N | ex. 107 | $^1$H NMR (200 MHz, CDCl$_3$): 8.5(s, 3H); 7.35 to 7.15(m, 2H); 7.0 to 6.75(m, 3H); 3.9 (t, 2H, J=6 Hz); 3.45 to 3.2(m, 1H); 3.05 to 2.7(m, 2H); 2.0(t, 1H, J=8 Hz); 1.95 to 1.15(m, 12H) |
| 191 (RS) | (　)₄-O-C₆H₄-CF₃, SH, HCl, H₂N | ex. 110 | $^1$H NMR (200 MHz, CDCl$_3$): 8.5(s, 3H); 7.5 to 6.85(m, 4H); 3.9(t, 2H, J=6 Hz); 3.55 to 3.25(m, 1H); 3.15 to 2.7(m, 2H); 2.0(t, 1H, J=8 Hz); 2.0 to 1.4(m, 6H) |

-continued

| Ex. No. (conf.) | Compound | Starting material | Analyses |
|---|---|---|---|
| 192 (RS) | (structure with (CH2)4 chain, HCl·H2N, SH, O-phenyl-F) | ex. 111 | $^1$H NMR (200 MHz, CDCl$_3$): 8.5(s, 3H); 7.4 to 7.0(m, 1H); 6.8 to 6.4 (m, 3H); 3.8(t, 2H, J=6 Hz); 3.55 to 3.2(m, 1H); 3.1 to 2.65(m, 2H); 2.1 to 1.2 m, 7H) |
| 193 (RS) | (structure with (CH2)4 chain, HCl·H2N, SH, O-phenyl-2,4-F2) | ex. 112 | $^1$H NMR (200 MHz, CDCl$_3$): 8.5(s, 3H); 6.95 to 6.65(m, 3H); 3.9(t, 2H, J=6.5 Hz); 3.5 to 3.35(m, 1H); 3.0 to 2.75(m, 2H); 2.05 to 1.5(m, 7H) |
| 194 (RS) | (structure with (CH2)4 chain, HCl·H2N, SH, O-phenyl-2-F) | ex. 114 | $^1$H NMR (200 MHz, CDCl$_3$): 8.5(s, 3H); 7.1 to 6.7(m, 4H); 3.95(t, 2H, J=6 Hz); 3.55 to 3.25(m, 1H); 3.1 to 2.65(m, 2H); 2.0 (t, 1H, J=8 Hz); 2.0 to 1.4(m, 6H) |
| 195 (RS) | (structure with (CH2)4 chain, HCl·H2N, SH, O-perfluorophenyl) | ex. 117 | $^1$H NMR (200 MHz, CDCl$_3$): 8.5(s, 3H); 4.15(t, 2H, J=6 Hz); 3.6 to 3.3(m, 1H); 3.1 to 2.7(m, 2H); 2.0(t, 1H, J=8 Hz); 2.0 to 1.45(m, 6H) |
| 196 (RS) | (structure with (CH2)4 chain, HCl·H2N, SH, O-phenyl-4-NO2) | ex. 118 | $^1$H NMR (200 MHz, CDCl$_3$): 8.5(s, 3H); 8.1 and 6.85(AB, 4H, J=8.8 Hz); 3.95(t, 2H, J=6 Hz); 3.5 to 3.35(m, 1H); 3.05 to 2.7(m, 2H); 2.05 to 1.45(m, 7H) |
| 197 (RS) | (structure with (CH2)6 chain, Ph, HCl·H2N, SH) | ex. 143 | $^1$H NMR (200 MHz, CDCl$_3$): 8.4(broad s, 3H); 7.35 to 7.05(m, 5H); 3.45 to 3.2(m, 1H); 3.05 to 2.7(m, 2H); 2.55(t, 2H, J=7.4 Hz); 1.95(t, 1H, J=8 Hz); 1.95 to 1.15(m, 10H) |
| 198 (RS) | (structure with (CH2)4 chain, HCl·H2N, SH, O-phenyl-3,5-(OMe)2) | ex. 122 | $^1$H NMR (200 MHz, CDCl$_3$): 8.5(broad s, 3H); 6.05(s, 3H); 3.9(t, 2H, J=7.4 Hz); 3.7(s, 6H); 3.5 to 3.3(m, 1H); 3.05 to 2.75(m, 2H); 2.05 to 1.5(m, 7H). |
| 199 (RS) | (structure with (CH2)4 chain, HCl·H2N, SH, O-phenyl-4-On.Bu) | ex. 124 | $^1$H NMR (200 MHz, CDCl$_3$): 8.5(broad s, 3H); 6.8(s, 4H); 3.85(t, 4H, J=6.7 Hz); 3.45 to 3.25(m, 1H); 3.05 to 2.7(m, 2H); 2.05 to 1.3(m, 11H); 0.9(t, 3H, J=7 Hz). |
| 200 (RS) | (structure with (CH2)4 chain, HCl·H2N, SH, O-phenyl-3,4-Cl2) | ex. 123 | $^1$H NMR (200 MHz, CDCl$_3$): 8.45(broad s, 3H); 7.35 to 7.2(m, 1H); 7.0 to 6.9(m, 1H); 6.8 to 6.6(m, 1H); 3.85(t, 2H, J 6.7 Hz); 3.5 to 3.25 (m, 1H); 3.05 to 2.75(m, 2H); 2.05 to 1.4(m, 7H). |
| 201 (RS) | (structure with (CH2)4 chain, 2HCl·H2N, SH, O-2-pyridyl) | ex. 125 | $^1$H NMR (D$_2$O, 200 MHz): 7.8 to 7.45(m, 2H); 6.75 to 6.45(m, 2H); 3.9 (t, 2H, J=6.7 Hz); 3.3 to 3.05(m, 1H); 2.8 to 2.35(m, 2H); 1.8 to 1.05 (m, 6H) |

-continued

| Ex. No. (conf.) | Compound | Starting material | Analyses |
|---|---|---|---|
| 202 (RS) | (structure with (CH₂)₄, O-phenyl-CN, SH, HCl·H₂N) | ex. 151 | ¹H NMR (CDCl₃, 200 MHz): 8.5(broad s, 3H); 7.4 to 7.0(m, 4H); 3.95 (t, 2H, J=6.7 Hz); 3.65 to 3.3(m, 1H); 3.1 to 2.75(m, 2H); 2.05(t, 1H, J=7.4 Hz); 2.15 to 1.4(m, 6H) |
| 203 (RS) | (structure with (CH₂)₃, O-phenyl-CH₂Ph, SH, HCl·H₂N) | ex. 126 | ¹H NMR (CDCl₃, 200 MHz): 8.55(broad s, 3H); 7.4 to 7.1(m, 5H); 7.05 and 6.8(AB, 4H, J=8.4 Hz); 4.05 to 3.8(m, 2H); 3.6 to 3.35(m, 1H); 3.1 to 2.6(m, 2H); 2.15 to 1.55(m, 5H). |
| 204 (RS) | (structure with (CH₂)₄, O-phenyl-Cl, SH, HCl·H₂N) | ex. 127 | ¹H NMR (CDCl₃, 200 MHz): 8.5(broad s, 3H); 7.3 to 7.05(m, 1H); 7.0 and 6.65(m, 3H); 3.9(t, 2H, J=6.7 Hz); 3.55 to 3.25(m, 1H); 3.1 to 2.6 (m, 2H); 2.0(t, 1H, J=8.4 Hz); 2.0 to 1.4(m, 6H). |
| 205 (RS) | (structure with (CH₂)₅, O-phenyl-CN, SH, HCl·H₂N) | ex. 152 | ¹H NMR (CDCl₃, 200 MHz): 8.5(broad s, 3H); 7.55 and 6.9(AB, 4H, X=9.6 Hz); 3.95(t, 2H, J=6 Hz); 3.5 to 3.25(m, 1H); 3.05 to 2.7(m, 2H); 2.0(t, 1H, J=7.4 Hz); 1.95 to 1.3(m, 8H). |
| 206 (RS) | (structure with (CH₂)₃, O-phenyl-CN, SH, HCl·H₂N) | ex. 153 | ¹H NMR (CDCl₃, 200 MHz): 8.55(broad s, 3H); 7.5 and 6.85(AB, 4H, X=7.4 Hz); 4.15 to 3.8(m, 2H); 3.7 to 3.35(m, 1H); 3.15 to 2.7(m, 2H); 2.2 to 1.75(m, 5H). |
| 207 (RS) | (structure with (CH₂)₄, O-phenyl-Et, SH, HCl·H₂N) | ex. 128 | ¹H NMR (CDCl₃, 200 MHz): 8.5(broad s, 3H); 7.25 to 7.1(m, 1H); 6.8 to 6.6(m, 3H); 3.9(t, 2H, J=6.7 Hz); 3.5 to 3.25(m, 1H); 3.05 to 2.7 (m, 2H); 2.6(q, 2H, J=7.4 Hz); 2.05 to 1.5(m, 7H); 1.2(t, 3H, J=6.7 Hz). |
| 208 (RS) | (structure with (CH₂)₄, O-phenyl-CF₃, SH, HCl·H₂N) | ex. 129 | ¹H NMR (CDCl₃, 200 MHz): 8.5(broad s, 3H); 7.5 and 6.9(AB, 4H, X=7.4 Hz); 3.95(t, 2H, J=6.7 Hz); 3.5 to 3.25(m, 1H); 3.1 to 2.7(m, 2H); 2.1 to 1.5(m, 7H). |
| 209 (RS) | (structure with (CH₂)₄, O-phenyl-CH₂Ph, SH, HCl·H₂N) | ex. 130 | ¹H NMR (CDCl₃, 200 MHz): 8.5(broad s, 3H); 7.5 to 7.0(m, 7H); 6.85 to 6.7(m, 2H); 3.95 to 3.75(m, 4H); 3.5 to 3.3(m, 1H); 3.0 to 2.75(m, 2H); 2.05 to 1.35(m, 9H). |
| 210 (RS) | (structure with (CH₂)₄, O-phenyl-CH₂Ph, SH, HCl·H₂N) | ex. 131 | ¹H NMR (CDCl₃, 200 MHz): 8.45(broad s, 3H); 7.3 to 7.0(m, 7H); 6.85 to 6.71(m, 2H); 4.0 to 3.75(m, 4H); 3.45 to 3.25(m, 1H); 3.0 to 2.7(m, 2H); 2.05 to 1.40(m, 7H). |
| 211 (RS) | (structure with (CH₂)₃, O-phenyl-Et, SH, HCl·H₂N) | ex. 132 | ¹H NMR (CDCl₃, 200 MHz): 8.45(broad s, 3H); 7.2 to 7.1(m, 1H); 6.8 to 6.65(m, 3H); 3.9(t, 2H, J=6.7 Hz); 3.5 to 2.25(m, 1H); 3.1 to 2.7 (m, 2H); 2.55(q, 2H, J=7.4 Hz); 2.05 to 1.5(m, 9H); 1.15(t, 3H, J=6.7 Hz). |
| 212 (RS) | (structure with (CH₂)₃, O-phenyl-CH₃, SH, HCl·H₂N) | ex. 133 | ¹H NMR (CDCl₃, 200 MHz): 8.5(s, 3H); 7.05 and 6.75(AB, 4H, X=7.4 Hz); 4.05 to 3.8(m, 2H); 3.65 to 3.35(m, 1H); 3.1 to 2.75(m, 2H); 2.2 (s, 3H); 2.15 to 1.75(m, 5H). |

| Ex. No. (conf.) | Compound | Starting material | Analyses |
|---|---|---|---|
| 213 (RS) | HCl, H₂N-(⋅)₄-O-C₆H₄-NH-C(O)CH₃ with SH | ex. 134 | $^1$H NMR (DMSO-d6, 200 MHz); 9.9(s, 1H); 8.45 to 7.75(m, 4H); 7.45 and 6.85(AB, 4H, X=8.4 Hz); 3.9(t, 2H, J=6.7 Hz); 3.3 to 3.0(m, 1H); 3.0 to 2.65(m, 2H); 1.95(s, 3H); 1.8 to 1.3(m, 6H) |
| 214 (RS) | HCl, H₂N-(⋅)₄-O-C₆H₄-I with SH | ex. 135 | $^1$H NMR (DMSO-d6, 200 MHz): 8.1(s, 3H);7.5 and 6.65(AB, 4H, X=8.4 Hz); 3.9(t, 2H, J=6.7 Hz); 3.3 to 3.1(m, 1H); 2.9 to 2.65(m, 3H); 1.8 to 1.3(m, 6H). |
| 215 (RS) | HCl, H₂N-(⋅)₄-O-C₆H₄-On.Pr with SH | ex. 136 | $^1$H NMR (CDCl₃, 200 MHz): 8.5(broad s, 3H); 6.8(s, 4H); 3.95 to 3.75 (m, 4H); 3.5 to 3.3(m, 1H); 3.0 to 2.75(m, 2H); 2.05 to 1.5(m, 9H); 0.9 (t, 3H, J=7.4 Hz). |
| 216 (RS) | HCl, H₂N-(⋅)₃-O-C₆H₄-C(O)Ph with SH | ex. 137 | $^1$H NMR (CDCl₃, 200 MHz): 8.5(broad s, 3H); 7.85 to 7.25(m, 7H); 7.0 to 6.65(m, 2H); 4.15 to 3.9(m, 2H); 3.6 to 3.4(m, 1H); 3.1 to 2.5(m, 2H); 2.2 to 1.7(m, 5H). |
| 217 (RS) | HCl, H₂N-(⋅)₃-O-C₆H₄-OEt with SH | ex. 138 | $^1$H NMR (CDCl₃, 200 MHz): 8.5(broad s, 3H); 6.75(s, 4H); 3.95(q, 2H, J=6.7 Hz); 4.0 to 3.8(m, 2H); 3.6 to 3.35(m, 1H); 3.05 to 2.75(m, 2H); 2.05(t, 1H, J=8.2 Hz); 2.1 to 1.75(m, 4H); 1.35(t, 3H, J=6.7 Hz). |
| 218 (RS) | HCl, H₂N-(⋅)₅-O-C₆H₄-OEt with SH | ex. 139 | $^1$H NMR (CDCl₃, 200 MHz): 8.5(broad s, 3H); 6.75(s, 4H); 3.9(q, 2H, J=6.7 Hz); 3.85(t, 2H, J=6.7 Hz); 3.5 to 3.25(m, 1H); 3.0 to 2.7(m, 2H); 2.0(t, 1H, J=8.2 Hz); 1.95 to 1.35(m, 8H); 1.35(t, 3H, J=6.7 Hz). |

Example 219

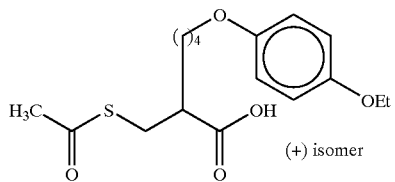

(+) isomer

A solution of 9.70 g (58.82 mmol) of (1R,2S)-(−)-ephedrine in 50 ml of ethyl ether is added to a solution of 20 g (58.82 mmol) of the racemic acid of Example 115 in 200 ml of ethyl ether. The stirring is maintained for 18 hours at room temperature.

The medium is filtered and the salt is washed with 100 ml of ethyl ether. After drying under vacuum, 15.01 g (50%) of a white salt are obtained.

$[\alpha]_D^{20} = -1.3°$ (c=1.5 in CHCl₃).

This salt is then recrystallized by dissolving in 40 ml of dichloromethane and 300 ml of ethyl ether at room temperature. The stirring is maintained overnight at room temperature.

The medium is filtered, washed with ethyl ether and dried under vacuum. 6.84 g (86%) of salt are obtained.

$[\alpha]_D^{21} = +4.7°$ (c=1.2 in CHCl₃).

The recrystallization is repeated again 5 times in order to obtain a stable optical rotation.

Overall yield of 6 recrystallizations: 33%.

Optical rotation of the final salt: $[\alpha]_D^{21} = +7.8°$ (c=1.2 in CHCl₃).

An N solution of HCl is added, at about 5° C., to a solution of 5.1 g (10.1 mmol) of optically pure salt (+) in 30 ml of dichloromethane, to pH=1. The organic phase is washed with 10 ml of water and dried over MgSO₄, filtered and concentrated under vacuum. 3.26 g (95%) of a white solid are thus obtained.

m.p.=+64° C.

$[\alpha]_D^{22} = +26.3°$ (c=1.4 in CHCl₃).

Overall resolution yield: 16%.

Example 220

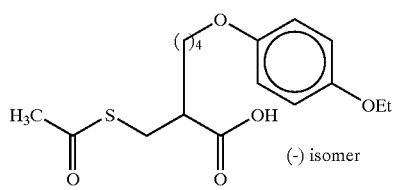

(−) isomer

The racemic acid of Example 115 is resolved with (1S, 2R)-(+)-ephedrine in ethyl ether as described in Example 119.

Yield: 63%

$[\alpha]_D^{22} = 1.1°$ (c=1.2 in CHCl₃).

The salt is then recrystallized 5 times in a mixture of dichloromethane and ethyl ether according to the same procedure as described in Example 119.

Overall yield of 5 recrystallizations: 36%.

Optical rotation of the final salt: $[\alpha]_D^{21}=-7.8°$ (c=1.2 in CHCl$_3$).

The acid is then released as described in Example 219.

Yield: 97%.

m.p.:=64° C.

$[\alpha]_D^{21}=-26.2°$ (c=1.4 in CHCl$_3$).

Overall resolution yield: 22%.

Example 221

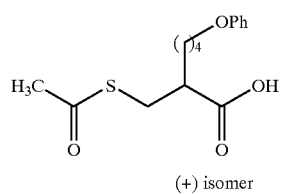

(+) isomer

The (+) isomer is obtained according to the same reaction sequence as that described in Example 219, but starting with the racemic acid of Example 89 and (1R,2S)-(−)-ephedrine.

Optical rotation of the salt obtained after the resolution step: $[\alpha]_D^{21}=5.6°$ (c=1.2 in CHCl$_3$).

Optical rotation of the salt obtained after 6 recrystallizations: $[\alpha]_D^{21}=+6.1°$ (c=1.2 in CHCl$_3$).

Optical rotation of the free acid: $[\alpha]_D^{21}=+26.4°$ (c=1.2 in CHCl$_3$).

Melting point of the (+) acid: <50° C.

Overall resolution yield: 12%.

Example 222

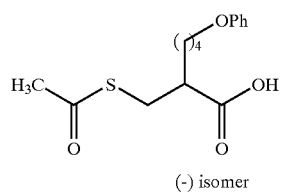

(−) isomer

The (−) isomer is obtained according to the same reaction sequence as that described in Example 220 but starting with the racemic acid of Example 89 and (1S,2R)-(+)-ephedrine.

Optical rotation of the salt obtained after the resolution step: $[\alpha]_D^{21}=+6.1°$ (c=1.2 in CHCl$_3$).

Optical rotation of the salt after 8 recrystallizations: $[\alpha]_D^{21}=-8.3°$ (c=1.2 in CHCl$_3$).

Optical rotation of the free acid: $[\alpha]_D^{21}=-29.6°$ (c=1.2 in CHCl$_3$).

Melting point of the (−) acid: <50° C.

Overall resolution yield: 10%

Examples 223 to 226 are prepared according to the same method as that described in Example 183.

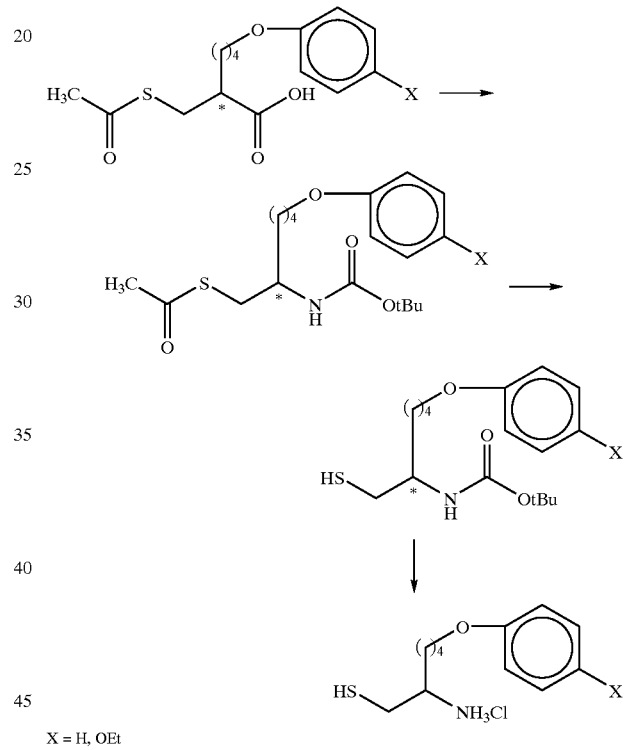

X = H, OEt

| Ex. No. (sign) | Compound | Starting material | $[\alpha]_D$ | m. p. (° C.) |
|---|---|---|---|---|
| 223 (+) | HCl, H$_2$N—*—SH—⟨phenyl⟩—O—(CH$_2$)$_4$—OEt | ex. 219 | $[\alpha]_D^{24} = +4.7°$ (C = 1 in CHCl$_3$) | 128 |
| 224 (−) | HCl, H$_2$N—*—SH—⟨phenyl⟩—O—(CH$_2$)$_4$—OEt | ex. 220 | $[\alpha]_D^{24} = -4.5°$ (C = 1 in CHCl$_3$) | 129 |

| Ex. No. (sign) | Compound | Starting material | $[\alpha]_D$ | m. p. (° C.) |
|---|---|---|---|---|
| 225 (+) | 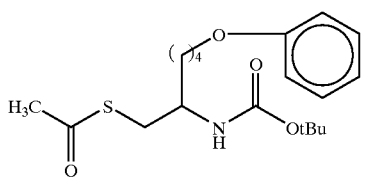 | ex. 221 | $[\alpha]_D^{22}$ = +3.8° (C = 1.1 in CHCl$_3$) | 98 |
| 226 (−) | 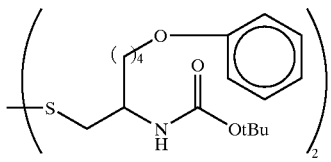 | ex. 222 | $[\alpha]_D^{22}$ = −4.5° (C = 1.1 in CHCl$_3$) | 100 |

Example 227

The acid of Example 89 is treated with DPPA, NEt$_3$ and tert-butyl alcohol according to the same method as that described in Example 181.

Example 228

11.1 ml of 1 N NaOH are added at 0° C. to a solution of 2.05 g (5.58 mmol) of the carbamate of Example 227 in 10 ml of EtOH. The medium is stirred overnight at room temperature. 10 ml of a 0.3 M solution of iodine in ethanol are added. The solvents are evaporated off and the residue is taken up in 50 ml of Et$_2$O. The medium is washed with water (once 20 ml), with a saturated aqueous sodium thiosulphate solution (twice 20 ml) and with a saturated aqueous NaCl solution (once 15 ml). The medium is dried over MgSO$_4$, filtered and concentrated. 1.85 g of a white solid are obtained, which solid is chromatographed on silica (eluent: ether-petroleum ether 2/8). 1.5 g (yield 84%) of a white solid are obtained.

Example 229

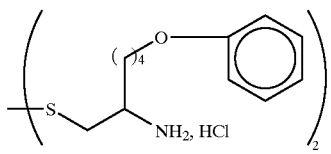

The carbamate of Example 228 is treated with gaseous HCl in MeOH according to the same method as that described in Example 183.

$^1$H NMR (DMSO-d6, 200 MHz): 8.3 (broad s, 3H); 7.35 to 7.1 (m, 2H); 7.0 to 6.75 (m, 3H); 3.9 (t, 2H, J=5 Hz); 3.6 to 3.5 (m, 1H); 3.2 to 2.95 (m, 2H); 1.95 to 1.35 (m, 6H).

Examples 230 to 236 are prepared according to the same method as that described for Example 229.

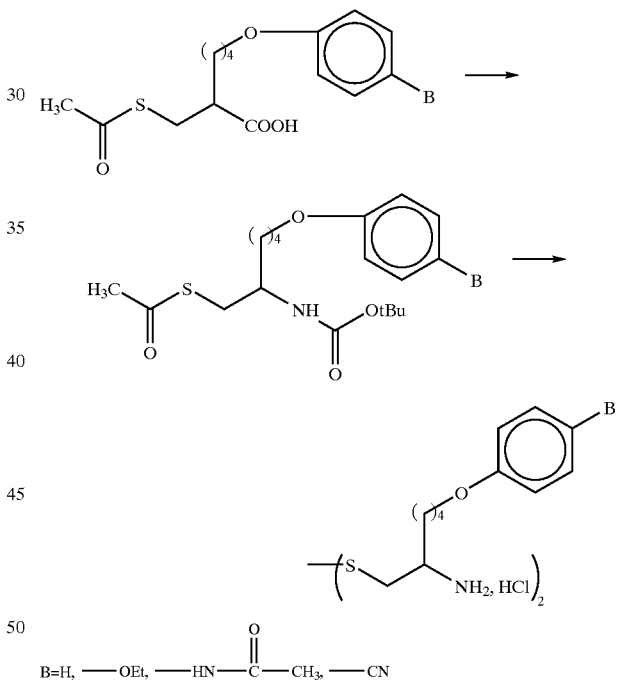

B=H, ——OEt, ——HN—C(=O)—CH$_3$, ——CN

| ex n° | configuration | B | Starting material | $[\alpha]_D$ |
|---|---|---|---|---|
| 230 | (+)-isomer A | H | ex. 222 | +29.8° (c = 0.4; CHCl$_3$) |
| 231 | (−)-isomer B | H | ex. 221 | −29.5° (c = 0.4; CHCl$_3$) |
| 232 | (RS, RS) | OEt | ex. 115 | / |
| 233 | (+)-isomer A | OEt | ex. 220 | +28.4° (c = 0.3; CHCl$_3$) |
| 234 | (−)-isomer B | OEt | ex. 219 | −28.9° (c = 0.4; CHCl$_3$) |

-continued

| ex n° | configuration | B | Starting material | $[\alpha]_D$ |
|---|---|---|---|---|
| 235 | (RS, RS) | NC—C(=O)—CH$_3$ | ex. 134 | / |
| 236 | (RS, RS) | CN | ex. 150 | / |

Example 237

The acid of Example 89 is treated with DPPA, NEt$_3$ and benzyl alcohol according to the same method as that described in Example 9.

Example 238

0.5 g (1.24 mmol) of the carbamate of Example 230 is dissolved in 6 ml of a 30% hydrobromic acid solution in acetic acid. The medium is stirred for 15 minutes at room temperature and then evaporated to dryness. After trituration in ethyl ether, the oily residue is dried under vacuum over P$_2$O$_5$.

0.3 g (70%) of an oil is obtained. $^1$H NMR (CDCl$_3$, 200 MHz): 8.2 (broad s, 3H); 7.3 to 7.15 (m, 2H); 6.95 to 6.75 (m, 3H); 3.9 (t, 5 Hz, 2H); 3.65 to 3.05 (m, 3H); 2.3 (s, 3H); 2.2 to 1.5 (m, 6H).

Biological Activity

Biological Trials of the Compounds According to the Invention

1) Inhibition of the aminopeptidase activity of recombinant LTA$_4$ hydrolase

The compounds were tested using human recombinant LTA$_4$ hydrolase (Minami et al., FEBS Letters, 1988, 229: 279). The LTA$_4$ hydrolase expressed by *E. coli* JM109 is purified mainly according to Minami et al., (J. Biol. Chem., 1987, 262: 13873).

The inhibition of the aminopeptidase activity of the enzyme is measured by means of a fluorimetric method in 96-well microplates. The recombinant enzyme (0.5 μg in 50 μl of 50 mM Tris-HCl pH 7.4) is preincubated for 10 minutes at 37° C. in the presence of inhibitor and of dithiothreitol (DTT, 10$^{-5}$ M). The substrate alanyl-amido-methylcoumarin (Ala-AMC, 25 μM–Tris HCl 50 mM, pH 7.4) is added and the incubation is continued for 15 minutes at 37° C. The release of AMC is measured by fluorimetry.

To evaluate the specificity of the compounds according to the invention, some of them were also tested for their capacity to inhibit the activity of membrane aminopeptidase M (EC 3.4.11.2). The same test is carried out with 0.1 μg of aminopeptidase M (Pierce, USA).

Typical results are given in Table I below:

TABLE I

INHIBITION OF LTA$_4$ HYDROLASE IN VITRO

| Compound No. | Inhibition of the aminopeptidase activity of LTA$_4$ hydrolase Ki | Inhibition of aminopeptidase M Ki |
|---|---|---|
| 23 | 62 nM | — |
| 172 | 15 nM | — |
| 173 | 33 nM | 0.2 μM |

2) Inhibition of the biosynthesis of LTB$_4$ in vitro

The biosynthesis of LTB$_4$ is measured in human whole blood in the presence of inhibitors of LTA$_4$ hydrolase according to the invention. A 50 μl blood sample collected over sodium heparinate is preincubated for 10 minutes at 37° C. in the presence of inhibitor (50 mM Tris-HCl, 0.15 M NaCl, 10$^{-5}$ M DTT, pH 7.4).

The LTA$_4$ substrate was freshly prepared by alkaline hydrolysis of LTA$_4$ methyl ester (Cayman Chemical Co., USA). After incubating for 10 minutes in the presence of LTA$_4$ (1 μm in 50 mM Tris-HCl, 0.15 M NaCl, 0.5% BSA, pH 7.4), the reaction is stopped by diluting 1/20 in 0.1 M potassium phosphate buffer containing 1.5 mM NaN$_2$, 0.4 M NaCl, 1 mM EDTA, 0.1% BSA, pH 7.4–4° C.

The LTB$_4$ is assayed by enzyme-linked immunoassay (Cayman Chemical Co, USA).

The results are given in Table II below.

TABLE II

INHIBITION OF THE BIOSYNTHESIS OF LTB$_4$ IN VITRO

| Compound No. | Inhibition of the LTA$_4$ hydrolase activity in human whole blood Ki |
|---|---|
| 172 | 190 nM |
| 173 | 200 nM |

3) Inhibition of the biosynthesis of LTB$_4$ ex vivo

The compounds inhibiting LTA$_4$ hydrolase according to the invention are suspended in 1.25% methyl cellulose and administered to mice by the oral route at the dose of 10 mg/kg. Thirty minutes later, the mice are sacrificed and the blood collected over lithium heparinate. The blood is then, as above, incubated for 10 minutes at 37° C. in the presence of LTA$_4$ and then the LTB$_4$ formed is assayed by enzyme-linked immunoassay.

The results obtained are indicated in Table III below:

TABLE III

INHIBITION OF THE BIOSYNTHESIS OF $LTB_4$ EX VIVO

| Compound No. | Inhibition (%) |
|---|---|
| 24 | 28 |
| 177 | 68 |

4) Anti-inflammatory activity a) Oedema of the leg induced by Zymosan in mice

Zymosan is a polysaccharide of the yeast cell membrane. Injected into the leg of animals, it causes a local inflammatory reaction in the form of an oedema. One hour after administration of the inhibitor tested by the oral route to mice, at the dose of 30 mg/kg, 25 µl of zymosan (0.05% in 0.15 M NaCl) are injected into the left hind leg and 25 µl of physiological saline into the right leg as control. The animal is sacrificed after 4 hours, the legs cut at the ankle and weighed in order to evaluate the oedema developed.

The results are given in Table IV below:

TABLE IV

INHIBITORY EFFECT ON OEDEMA OF THE LEG INDUCED BY ZYMOSAN

| Compound No. | Inhibition (%) |
|---|---|
| 156 | 35 | b) Inflammation induced by carrageenan in the air pouch model in mice

The air pouches are formed in mice according to Dawson et al. (Int. J. Tiss. React., 1991, XIII: 171). On day D, 5 ml of air are injected by the subcutaneous route into the back of the mice. On D+3, the pouch is maintained by reinjecting 3 ml of air. On D+6, either a cyclooxygenase inhibitor (indomethacin 5 mg/kg), or an $LTA_4$ hydrolase inhibitor according to the invention (25 mg/kg), or the two in combination are administered by the oral route. After 1 h, 1 ml of 1% carrageenan is injected into the air pouch. The animals are sacrificed 4 h after the injection of carrageenan. The air pouche is washed with 1 ml of 50 mM potassium phosphate buffer containing 0.15 M NaCl, pH 7.4. The exudate is recovered and centrifuged at 10,000 g for 5 minutes. $LTB_4$ is assayed in the supernatant by enzyme-linked immunoassay.

The results are indicated in Table V below:

TABLE V

INHIBITION OF THE BIOSYNTHESIS OF $LTB_4$ IN THE AIR POUCH MODEL IN MICE (inflammation by carrageenan)

| Treatment | % $LTB_4$ relative to the noninflamed control |
|---|---|
| Carrageenan | +87% |
| Carrageenan + indomethacin | +516% |
| Carrageenan + compound No. 156 | −24% |
| Carrageenan + indomethacin + compound No. 156 | −28% | c) Antiarthritic effect

Collagen-induced arthritis was induced in the rat "Dark Aganti" according to the protocol by Kamada et al. (Jpn J. Pharmacol., 1997, 74: 313). The $LTA_4$ hydrolase inhibitors are administered either "preventively" (starting from one day after the collagen), or curatively (during the first pathological manifestations, that is starting from 15 days after the collagen). The results in Table VI report the effect of compound No. 229 administered twice/day by the i.p. route, at the dose of 10 mg/kg on the arthritis score at the 23rd day after collagen. The effect is-compared with that of indomethacin (1.5 mg/kg, p.o.).

The results are indicated in Table VI below:

TABLE VI

| Treatment | Score |
|---|---|
| Vehicle | 3.1 ± 0.90 |
| Compound 229 (curative) | 0.38 ± 0.19 |
| Compound 229 (preventive) | 0 |
| Indomethacin (curative) | 1.35 ± 0.61 |

Moreover, the compounds according to the invention, in particular the compounds of formula (ii) or (iii), exhibit good bioavailability, higher than that of compounds known in the art, in particular from document WO 94/00420.

What is claimed is:

1. A compound of formula (I):

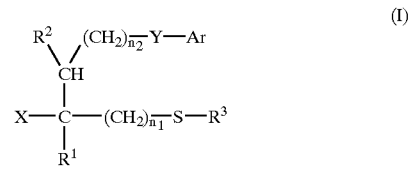

in which:

X is chosen from the following groups:
i) —$NH_2$ ii)
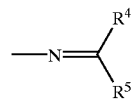

$R^1$ and $R^2$ are independently chosen from the following groups:
i) a hydrogen atom
ii) a lower alkyl group
iii a lower alkyl group substituted with a halogen atom
iv) $CF_3$
v) a halogen atom;

$n_1$ varies from 1 to 4

$n_2$ varies from 0 to 10

$R^3$ is chosen from the following groups:
i) a hydrogen atom ii)
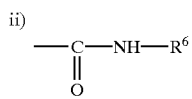

iii)
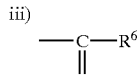

-continued iv)
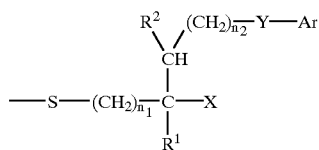

v)
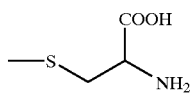

Y is chosen from the following groups:
i) —O—
ii) —$CH_2$—
iii) —S—
iv) —$OCH_2$—
v) —$SCH_2$—

Ar is chosen from the following groups:
i) a phenyl group which is unsubstituted or which is mono- or polysubstituted with substituents chosen from halogen atoms and $CF_3$, lower alkyl, lower alkoxy, $NH_2$, $NO_2$, CN, OH, $CO_2H$, OPh, $OCH_2Ph$, SMe, SEt, Ph, $CH_2Ph$ and $NHCOR^7$ groups where $R^7$ is a lower alkyl group, ii)
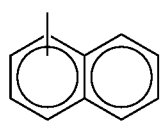

iii)

iv)
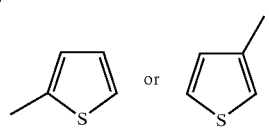

v)
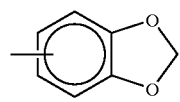

vi)
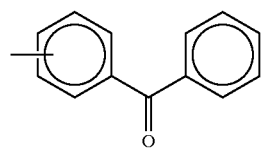

$R^4$ and $R^5$ are independently chosen from the following groups: an unsubstituted phenyl group, a phenyl group which is mono- or polysubstituted with substituents chosen from halogen atoms and $CF_3$, $NO_2$, CN, OH, lower alkyl and lower alkoxy groups;

$R^6$ represents a lower alkyl group or a phenyl group; excluding the compounds of formula I in which X is —$NH_2$, $R^1$ and $R^2$ are each a hydrogen atom, $n_1=1$, $n_2=0$, $R^3$ is a hydrogen atom or formula (v), Y is a group —$OCH_2$— or —$SCH_2$— and Ar is a phenyl group, as well as their isomers, diastereoisomers and enantiomers and their pharmaceutically acceptable salts.

2. The compound according to claim 1, wherein $R^1$ represents a hydrogen atom.

3. The compound according to claim 1, wherein $R^1$ is different from hydrogen.

4. The compound according to claim 1, wherein $n_1$ is equal to 1.

5. The compound according to claim 1, wherein $n_1$ is different from 1.

6. The compound according to claim 1, of formula (II):

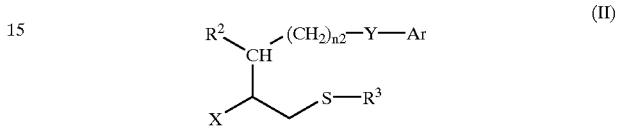

(II)

in which X, $R^2$, $R^3$, Y, Ar and $n_2$ have the meanings given in claim 1.

7. The compound according to claim 1, wherein X represents $NH_2$.

8. The compound according to claim 1, wherein $R^3$ represents a hydrogen atom.

9. The compound according to claim 1, wherein $R^2$ is different from a hydrogen atom.

10. The compound according to claim 1, wherein $R^2$ is a hydrogen atom.

11. The compound according to claim 1, of formula (III):

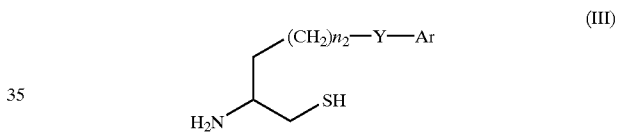

(III)

in which Y, Ar and $n_2$ have the meanings indicated in claim 1.

12. The compound according to claim 1, wherein $n_2$ is equal to zero.

13. The compound according to claim 1, wherein $n_2$ varies from 1 to 4.

14. The compound according to claim 1, wherein $n_2$ is equal to 3.

15. The compound according to claim 1, wherein $n_2$ is greater than 4.

16. The compound according to claim 1, wherein Y represents an oxygen atom.

17. The compound according to claim 1, wherein Y represents —$CH_2$—.

18. The compound according to claim 1, wherein Y represents a sulphur atom.

19. The compound according to claim 1, wherein Y represents —$OCH_2$— or —$SCH_2$—.

20. The compound according to claim 1, wherein $n_2$ is equal to zero and Y is chosen from —O—, —S—, —$OCH_2$— and —$SCH_2$—.

21. The compound according to claim 1, wherein Ar represents an unsubstituted phenyl group.

22. The compound according to claim 1, wherein Ar represents a substituted phenyl group.

23. The compound according to claim 1, wherein Ar represents a phenyl group which is mono- or polysubstituted with a group chosen from halogen atoms, $CF_3$, lower alkyl, O(lower alkyl), $NO_2$, CN, $CO_2H$, OPh, $OCH_2Ph$, Ph and $CH_2Ph$.

24. The compound according to claim 1, wherein Ar represents a phenyl group which is mono- or polysubstituted with a halogen atom or a lower alkyl or —O(lower alkyl) group.

25. The compound according to claim 1, wherein Ar represents a phenyl group which is substituted with a group —OPh, —OCH₂Ph, —Ph or —CH₂Ph.

26. The compound according to claim 1, wherein Ar represents a naphthyl group.

27. The compound according to claim 1, wherein Ar represents the group

28. The compound according to claim 1, wherein Ar represents the group

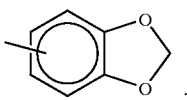

29. The compound according to claim 1, wherein said compound is selected from the group consisting of:

—(S)-2-amino-3-phenoxy-1-propanethiol hydrochloride
(2S,3R)-2-amino-3-methyl-3-benzyloxy-1-propanethiol hydrochloride
(2R,3S)-2-amino-3-methyl-3-benzyloxy-1-propanethiol hydrochloride
(R,S)-2-amino-7-phenyl-1-heptanethiol hydrochloride
(R,S)-2-amino-2-methyl-6-phenoxy-1-hexanethiol hydrochloride
(S)-2-amino-3-(4-benzylphenoxy)-1-propanethiol hydrochloride
(R,S)-2-amino-4-phenyl-1-butanethiol hydrochloride
(R,S)-2-amino-6-phenoxy-1-hexanethiol hydrochloride
(R,S)-2-amino-7-phenoxy-1-heptanethiol hydrochloride
(R,S)-2-amino-7-(4-methoxyphenoxy)-1-heptanethiol hydrochloride
(R,S)-2-amino-6-(4-methoxyphenoxy)-1-hexanethiol hydrochloride
(R,S)-2-amino-6-(4-methylphenoxy)-1-hexanethiol hydrochloride
(R,S)-2-amino-6-(3-methylphenoxy)-1-hexanethiol hydrochloride
(R,S)-2-amino-6-(3-methoxyphenoxy)-1-hexanethiol hydrochloride
(R,S)-2-amino-6-(4-chlorophenoxy)-1-hexanethiol hydrochloride
(R,S)-2-amino-6-(4-bromophenoxy)-1-hexanethiol hydrochloride
(R,S)-2-amino-6-(4-fluorophenoxy)-1-hexanethiol hydrochloride
(R,S)-2-amino-6-(2-methoxyphenoxy)-1-hexanethiol hydrochloride
(R,S)-2-amino-6-phenylthio-1-hexanethiol hydrochloride
(R,S)-2-amino-6-(3,4-dioxymethylenephenoxy)-1-hexanethiol hydrochloride
(R,S)-2-amino-6-(4-ethoxyphenoxy)-1-hexanethiol hydrochloride
(R,S)-2-amino-6-(4-ethylphenoxy)-1-hexanethiol hydrochloride
(R,S)-2-amino-5-phenyl-1-pentanethiol hydrochloride
(R,S)-2-amino-4-phenoxy-1-butanethiol hydrochloride
(R,S)-2-amino-6-phenyl-1-hexanethiol hydrochloride
(R,S)-2-amino-4-phenylthio-1-butanethiol hydrochloride
(R,S)-2-amino-6-(2,6-dimethylphenoxy)-1-hexanethiol hydrochloride
(R,S)-2-amino-4-benzylthio-1-butanethiol hydrochloride
(R,S)-2-amino-5-phenoxy-1-pentanethiol hydrochloride
(R,S)-2-amino-6-(2-methylphenoxy)-1-hexanethiol hydrochloride
(R,S)-2-amino-6-(4-phenoxyphenoxy)-1-hexanethiol hydrochloride
(R,S)-2-amino-6-(4-carboxyphenoxy)-1-hexanethiol hydrochloride
(R,S)-2-amino-6-(4-cyanophenoxy)-1-hexanethiol hydrochloride
[2(R,S)-3(R,S)]-2-amino-3-methyl-6-phenoxy-1-hexanethiol hydrochloride
(R,S)-2-amino-6-(4-phenylphenoxy)-1-hexanethiol hydrochloride
(R,S)-2-amino-6-(4-benzyloxyphenoxy)-1-hexanethiol hydrochloride
(R,S)-2-amino-6-(2-naphthyloxy)-1-hexanethiol hydrochloride
(R,S)-2-amino-6-(1-naphthyloxy)-1-hexanethiol hydrochloride
(R,S)-2-amino-8-phenoxy-1-octanethiol hydrochloride
(R,S)-2-amino-9-phenoxy-1-nonanethiol hydrochloride
(R,S)-2-amino-6-(3-trifluoromethylphenoxy)-1-hexanethiol hydrochloride
(R,S)-2-amino-6-(3-fluorophenoxy)-1-hexanethiol hydrochloride
(R,S)-2-amino-6-(2,4-difluorophenoxy)-1-hexanethiol hydrochloride
(R,S)-2-amino-6-(2-fluorophenoxy)-1-hexanethiol hydrochloride
(R,S)-2-amino-6-pentafluorophenoxy-1-hexanethiol hydrochloride
(R,S)-2-amino-6-(4-nitrophenoxy)-1-hexanethiol hydrochloride
(R,S)-2-amino-8-phenyl-1-octanethiol hydrochloride
(R,S)-2-amino-6-(3,5-dimethoxyphenoxy)-1-hexanethiol hydrochloride
(R,S)-2-amino-6-(4-butoxyphenoxy)-1-hexanethiol hydrochloride
(R,S)-2-amino-6-(4,5-dichlorophenoxy)-1-hexanethiol hydrochloride
(R,S)-2-amino-6-(2-pyridoxy)-1-hexanethiol hydrochloride
(R,S)-2-amino-6-(3-cyanophenoxy)-1-hexanethiol hydrochloride
(R,S)-2-amino-5-(4-benzylphenoxy)-1-pentanethiol hydrochloride
(R,S)-2-amino-6-(3-chlorophenoxy)-1-hexanethiol hydrochloride
(R,S)-2-amino-7-(4-cyanophenoxy)-1-heptanethiol hydrochloride
(R,S)-2-amino-5-(4-cyanophenoxy)-1-pentanethiol hydrochloride
(R,S)-2-amino-6-(3-ethylphenoxy)-1-hexanethiol hydrochloride
(R,S)-2-amino-6-(4-trifluoromethylphenoxy)-1-hexanethiol hydrochloride
(R,S)-2-amino-7-(4-benzylphenoxy)-1-heptanethiol hydrochloride
(R,S)-2-amino-6-(4-benzylphenoxy)-1-hexanethiol hydrochloride
(R,S)-2-amino-5-(3-ethylphenoxy)-1-pentanethiol hydrochloride
(R,S)-2-amino-5-(4-methylphenoxy)-1-pentanethiol hydrochloride (R,S)-2-amino-6-(4-acetamidophenoxy)-1-hexanethiol hydrochloride
(R,S)-2-amino-6-(4-iodophenoxy)-1-hexanethiol hydrochloride
(R,S)-2-amino-6-(4-propoxyphenoxy)-1-hexanethiol hydrochloride
(R,S)-2-amino-5-(4-benzoylphenoxy)-1-pentanethiol hydrochloride
(R,S)-2-amino-5-(4-ethoxyphenoxy)-1-pentanethiol hydrochloride
(R,S)-2-amino-7-(4-ethoxyphenoxy)-1-heptanethiol hydrochloride
(+)-2-amino-6-(4-ethoxyphenoxy)-1-hexanethiol hydrochloride
(−)-2-amino-6-(4-ethoxyphenoxy)-1-hexanethiol hydrochloride
(+)-2-amino-6-phenoxy-1-hexanethiol hydrochloride
(−)-2-amino-6-phenoxy-1-hexanethiol hydrochloride.

30. The compound according to claim 1, wherein X represents the group

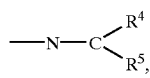

$R^4$ and $R^5$ being as defined in claim 1.

31. The compound according to claim 1, wherein $R^3$ represents the group

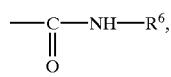

$R^6$ having the meaning given in claim 1.

32. The compound according to claim 1, wherein $R^3$ represents the group

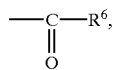

$R^6$ having the meaning given in claim 1.

33. The compound according to claim 1, wherein $R^3$ represents the group

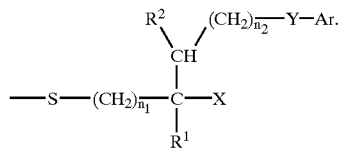

34. The compound according to claim 1, wherein $R^3$ represents the group

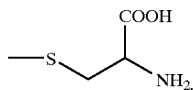

35. The compound according to claim 1, wherein said compound is selected from the group consisting of:
1,1-dithiobis(2-(R,S)-amino-6-phenoxyhexane) dihydrochloride
(R,S)-2-amino-6-phenoxy-1-S-acetylthiohexane hydrobromide
1,1-dithiobis(2-(+)-amino-6-phenoxyhexane) dihydrochloride (A isomer)
1,1-dithiobis(2-(−)-amino-6-phenoxyhexane) dihydrochloride (B isomer)
1,1-dithiobis(2-(R,S)-amino-6-(4-ethoxyphenoxy)-1-hexane) dihydrochloride
1,1-dithiobis(2-(+)-amino-6-(4-ethoxyphenoxy)-1-hexane) dihydrochloride (A isomer)
1,1-dithiobis(2-(−)-amino-6-(4-ethoxyphenoxy)-1-hexane) dihydrochloride (B isomer)
1,1-dithiobis(2-(R,S)-amino-6-(4-acetamidophenoxy)-1-hexane dihydrochloride
1,1-dithiobis(2-(R,S)-amino-6-(4-cyanophenoxy)-1-hexane dihydrochloride.

36. A pharmaceutical composition, comprising a compound according to claim 1, in combination with a physiologically acceptable vehicle or excipient.

37. A method for inhibiting the activity of $LTA_4$ hydrolase which comprises administering to a patient in need thereof, an effective amount of a compound according to claim 1.

38. A method for treating an inflammatory condition, which method comprises administering to a patient in need of such a treatment, an effective amount of a compound according to claim 1.

39. A method for treating an arthritic condition, which method comprises which method comprises administering to a patient in need of such a treatment, an effective amount of a compound according to claim 1.

40. A method for treating a psoriatic condition, which method comprises administering to a patient in need of such a treatment, an effective amount of a compound according to claim 1.

41. A method for treating a hepatic condition, which method comprises administering to a patient in need of such a treatment, an effective amount of a compound according to claim 1.

42. A method for blocking mitons which comprises administering to a patient in need thereof, an effective amount of a compound according to claim 1.

43. A method for treating an overproduction of $LTB_4$ induced in particular by a cyclooxygenase inhibitor, which method comprises administering in a patient in need of such a treatment, an effective amount of a compound according to claim 1.

44. A pharmaceutical composition, comprising a compound according to claim 1 and a cyclooxygenase inhibitor, in combination with a physiologically acceptable vehicle or excipient.

45. A compound according to claim 1, having the formula

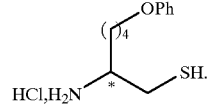

46. A compound according to claim 1, wherein $R^2$ represents a methyl group.

47. The compound according to claim 1, wherein $n_2$ varies from 2 to 4.

48. The compound according to claim 1, wherein Ar represents a monosubstituted phenyl group.

* * * * *

UNITED STATES PATENT AND TRADEMARK OFFICE
CERTIFICATE OF CORRECTION

PATENT NO. : 6,436,973 B1
DATED : August 20, 2002
INVENTOR(S) : Danvy et al.

It is certified that error appears in the above-identified patent and that said Letters Patent is hereby corrected as shown below:

<u>Column 2, line 1 through Column 3, line 42,</u>
Should be -- A compound of formula (I):

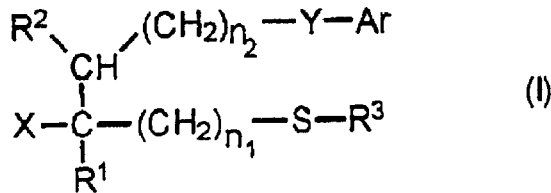

in which:
- X is chosen from the following groups:

i) $-NH_2$ ii) 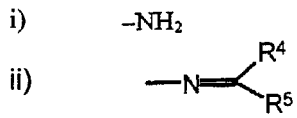

- $R^1$ and $R^2$ are independently chosen from the following groups:
    i) a hydrogen atom
    ii) a lower alkyl group
    iii) a lower alkyl group substituted with a halogen atom
    iv) $CF_3$
    v) a halogen atom;

- $n_1$ varies from 1 to 4
  $n_2$ varies from 0 to 10
  $R^3$ is chosen from the following groups:
      i) a hydrogen atom ii) 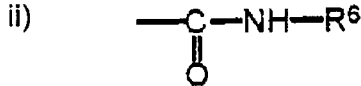

UNITED STATES PATENT AND TRADEMARK OFFICE
CERTIFICATE OF CORRECTION

PATENT NO. : 6,436,973 B1
DATED : August 20, 2002
INVENTOR(S) : Danvy et al.

It is certified that error appears in the above-identified patent and that said Letters Patent is hereby corrected as shown below:

iii) 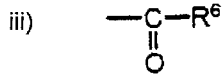

iv) 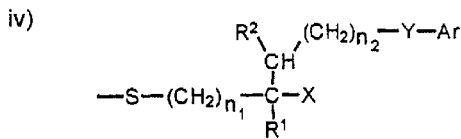

v) 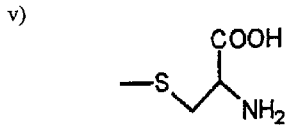

- Y is chosen from the following groups:
    i) -O-
    ii) -CH$_2$-
    iii) -S-
    iv) -OCH$_2$-
    v) -SCH$_2$-

- Ar is chosen from the following groups:
    i) a phenyl group which is unsubstituted or which is mono- or polysubstituted with substituents chosen from halogen atoms and CF$_3$, lower alkyl, lower alkoxy, NH$_2$, NO$_2$, CN, OH, CO$_2$H, OPh, OCH$_2$Ph, SMe, SEt, Ph, CH$_2$Ph and NHCOR$^7$ groups where R$^7$ is a lower alkyl group, ii) 

iii) 

UNITED STATES PATENT AND TRADEMARK OFFICE
CERTIFICATE OF CORRECTION

PATENT NO.    : 6,436,973 B1
DATED         : August 20, 2002
INVENTOR(S)   : Danvy et al.

It is certified that error appears in the above-identified patent and that said Letters Patent is hereby corrected as shown below:

iv) 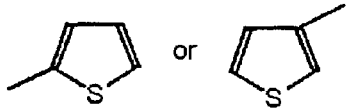

v) 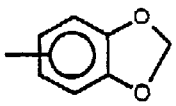

vi) 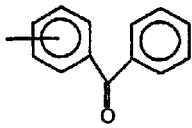

- $R^4$ and $R^5$ are independently chosen form the following groups: an unsubstituted phenyl group, a phenyl group which is mono- or polysubstituted with substituents chosen from halogen atoms and $CF_3$, $NO_2$, CN, OH, lower alkyl and lower alkoxy groups;
- $R^6$ represents a lower alkyl group or a phenyl group; excluding the compounds of formula I in which X is $-NH_2$, $R^1$ and $R^2$ are each a hydrogen atom, $n_1=1$, $n_2=0$, $R^3$ is a hydrogen atom, or formula (iv), Y is a group $-OCH_2-$ or $-SCH_2-$ and Ar is a phenyl group, as well as their isomers, diastereoisomers and enantiomers and their pharmaceutically acceptable salts. --

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,436,973 B1
DATED         : August 20, 2002
INVENTOR(S)   : Denis Danvy et al.

It is certified that error appears in the above-identified patent and that said Letters Patent is hereby corrected as shown below:

Column 2, line 1 through Column 3, line 42,

" The compounds according to the invention correspond to the following formula (I):

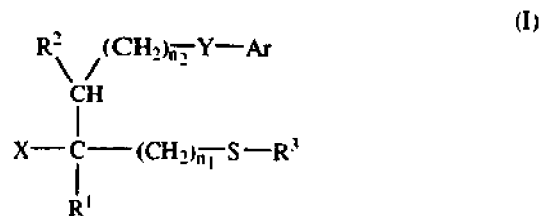

(I)

in which:
   X is chosen from the following groups:
      i) $-NH_2$ ii)
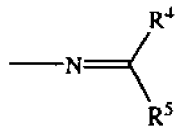

$R^1$ and $R^2$ are independently chosen from the following groups:
      i) a hydrogen atom
      ii) a lower alkyl group
      iii a lower alkyl group substituted with a halogen atom
      iv) $CF_3$
      v) a halogen atom;
   $n_1$ varies from 1 to 4
   $n_2$ varies from 0 to 10
   $R^3$ is chosen from the following groups:
      i) a hydrogen atom

UNITED STATES PATENT AND TRADEMARK OFFICE
CERTIFICATE OF CORRECTION

PATENT NO. : 6,436,973 B1
DATED : August 20, 2002
INVENTOR(S) : Denis Danvy et al.

It is certified that error appears in the above-identified patent and that said Letters Patent is hereby corrected as shown below:

Column 2, line 1 through Column 3, line 42 (cont'd), ii)
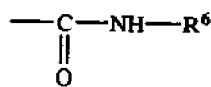

iii)
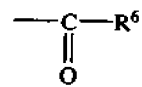

iv)
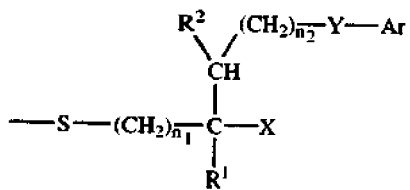

v)
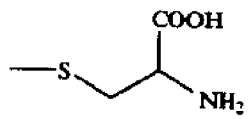

Y is chosen from the following groups:
i) —O—
  ii) —$CH_2$—
  iii) —S—
  iv) —$OCH_2$—
  v) —$SCH_2$—
  vi) —NH—

Ar is chosen from the following groups:
  i) a phenyl group which is unsubstituted or which is mono- or polysubstituted with substituents chosen from halogen atoms and $CF_3$, lower alkyl, lower alkoxy, $NH_2$, $NO_2$, CN, OH, $CO_2H$, OPh, $OCH_2Ph$, SMe, SEt, Ph, $CH_2Ph$ and $NHCOR^7$ groups where Column 2, line 1 through Column 3, line 42 (cont'd),
$R^7$ is a lower alkyl group,
ii)
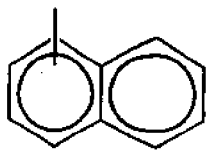
iii)
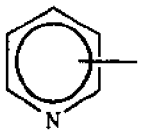
iv)
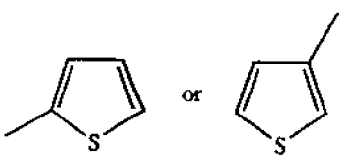 or
v)
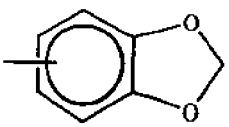
vi)
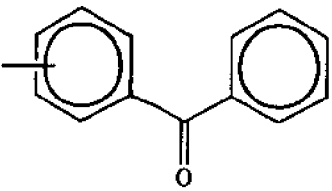

UNITED STATES PATENT AND TRADEMARK OFFICE
CERTIFICATE OF CORRECTION

PATENT NO. : 6,436,973 B1
DATED : August 20, 2002
INVENTOR(S) : Denis Danvy et al.

It is certified that error appears in the above-identified patent and that said Letters Patent is hereby corrected as shown below:

Column 2, line 1 through Column 3, line 42 (cont'd),

"$R^4$ and $R^5$ are independently chosen from the following groups: an unsubstituted phenyl group, a phenyl group which is mono- or polysubstituted with substituents chosen from halogen atoms and $CF_3$, $NO_2$, CN, OH, lower alkyl and lower alkoxy groups;
$R^6$ represents a lower alkyl group or a phenyl group.
The expression lower alkyl group is understood to mean an alkyl group having a linear or branched chain containing form 1 to 6 carbon atoms, such as methyl, ethyl, propyl, butyl, pentyl, hexyl and their branched isomers."

(as amended by Certificate of Correction issued April 1, 2003) is to be reinstated.

Column 99, line 25 to Column 100, line 4,
Should be:
1. A compound of formula (I):

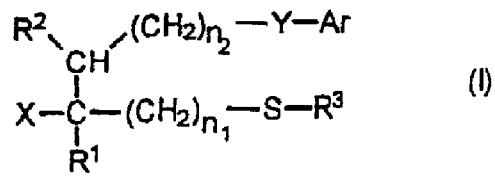

UNITED STATES PATENT AND TRADEMARK OFFICE
CERTIFICATE OF CORRECTION

PATENT NO. : 6,436,973 B1
DATED : August 20, 2002
INVENTOR(S) : Denis Danvy et al.

It is certified that error appears in the above-identified patent and that said Letters Patent is hereby corrected as shown below:

Column 99, line 25 to Column 100, line 4 (cont'd), in which:
- X is chosen from the following groups:

i)     $-NH_2$ ii) 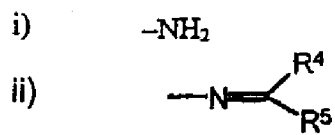

- $R^1$ and $R^2$ are independently chosen from the following groups:
    - i)    a hydrogen atom
    - ii)    a lower alkyl group
    - iii    a lower alkyl group substituted with a halogen atom
    - iv)    $CF_3$
    - v)    a halogen atom;
- $n_1$ varies from 1 to 4
- $n_2$ varies from 0 to 10
- $R^3$ is chosen from the following groups:
    - i)    a hydrogen atom

UNITED STATES PATENT AND TRADEMARK OFFICE
CERTIFICATE OF CORRECTION

PATENT NO. : 6,436,973 B1
DATED : August 20, 2002
INVENTOR(S) : Denis Danvy et al.

It is certified that error appears in the above-identified patent and that said Letters Patent is hereby corrected as shown below:

Column 99, line 25 to Column 100, line 4 (cont'd), ii) 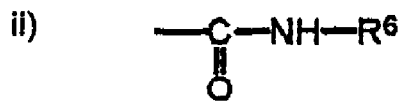

iii) 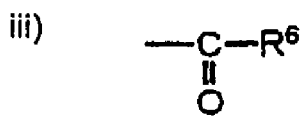

iv) 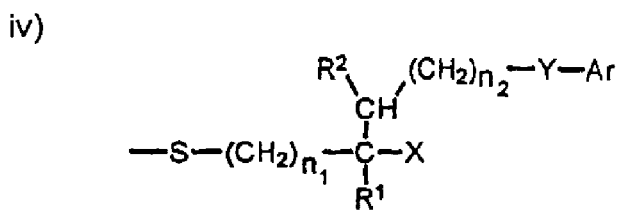

v) 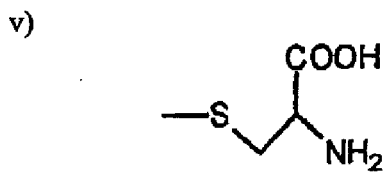

- Y is chosen from the following groups:
    i) -O-
    ii) -$CH_2$-
    iii) -S-
    iv) -$OCH_2$-
    v) -$SCH_2$-

UNITED STATES PATENT AND TRADEMARK OFFICE
CERTIFICATE OF CORRECTION

PATENT NO.    : 6,436,973 B1
DATED         : August 20, 2002
INVENTOR(S)   : Denis Danvy et al.

It is certified that error appears in the above-identified patent and that said Letters Patent is hereby corrected as shown below:

Column 99, line 25 to Column 100, line 4 (cont'd),

- Ar is chosen from the following groups:
    i) a phenyl group which is unsubstituted or which is mono- or polysubstituted with substituents chosen from halogen atoms and $CF_3$, lower alkyl, lower alkoxy, $NH_2$, $NO_2$, CN, OH, $CO_2H$, OPh, $OCH_2Ph$, SMe, SEt, Ph, $CH_2Ph$ and $NHCOR^7$ groups where $R^7$ is a lower alkyl group, ii) 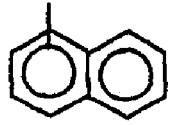

iii) 

iv) 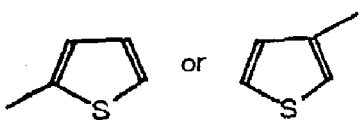

v) 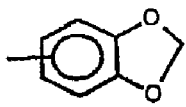

vi) 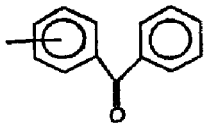

UNITED STATES PATENT AND TRADEMARK OFFICE
CERTIFICATE OF CORRECTION

PATENT NO. : 6,436,973 B1
DATED : August 20, 2002
INVENTOR(S) : Denis Danvy et al.

It is certified that error appears in the above-identified patent and that said Letters Patent is hereby corrected as shown below:

Column 99, line 25 to Column 100, line 4 (cont'd),

- $R^4$ and $R^5$ are independently chosen from the following groups: an unsubstituted phenyl group, a phenyl group which is mono- or polysubstituted with substituents chosen from halogen atoms and $CF_3$, $NO_2$, $CN$, $OH$, lower alkyl and lower alkoxy groups;
- $R^6$ represents a lower alkyl group or a phenyl group; excluding the compounds of formula I in which X is $-NH_2$, $R^1$ and $R^2$ are each a hydrogen atom, $n_1=1$, $n_2=0$, $R^3$ is a hydrogen atom, or formula (v), Y is a group $-OCH_2-$ or $-SCH_2-$ and Ar is a phenyl group, as well as their isomers, diastereoisomers and enantiomers and their pharmaceutically acceptable salts.

Signed and Sealed this

Third Day of May, 2005

JON W. DUDAS
*Director of the United States Patent and Trademark Office*